(12) United States Patent
Mao et al.

(10) Patent No.: US 11,793,535 B2
(45) Date of Patent: Oct. 24, 2023

(54) ENDOLUMINAL SURGERY DEVICE

(71) Applicant: Zhangfan Mao, Wuhan (CN)

(72) Inventors: Zhangfan Mao, Wuhan (CN); Hang Mao, Wuhan (CN)

(73) Assignee: Zhangfan Mao, Wuhan (CN)

(*) Notice: Subject to any disclaimer, the term of this patent is extended or adjusted under 35 U.S.C. 154(b) by 567 days.

(21) Appl. No.: 16/849,561

(22) Filed: Apr. 15, 2020

(65) Prior Publication Data

US 2020/0237390 A1 Jul. 30, 2020

Related U.S. Application Data

(63) Continuation of application No. PCT/CN2018/080972, filed on Mar. 28, 2018.

(30) Foreign Application Priority Data

Jun. 14, 2019 (CN) .......................... 201910517911.4

(51) Int. Cl.
*A61B 17/29* (2006.01)
*A61B 17/02* (2006.01)

(52) U.S. Cl.
CPC .......... *A61B 17/29* (2013.01); *A61B 17/0206* (2013.01); *A61B 17/0293* (2013.01);
(Continued)

(58) Field of Classification Search
CPC . A61B 17/0206; A61B 17/29; A61B 17/0293; A61B 2017/2901;
(Continued)

(56) References Cited

U.S. PATENT DOCUMENTS 9,554,819 B2 * 1/2017 Suzuki .................. A61B 17/29
10,835,217 B1 * 11/2020 Gomez .................. A61B 17/29
(Continued)

FOREIGN PATENT DOCUMENTS

CN 101827627 A 9/2010
CN 102357042 A 2/2012
(Continued)

OTHER PUBLICATIONS

International Search Report and Written Opinion for PCT/CN2018/080972, dated Dec. 28, 2018.
(Continued)

*Primary Examiner* — Wade Miles
*Assistant Examiner* — Bridget E. Rabaglia
(74) *Attorney, Agent, or Firm* — Andrus Intellectual Property Law, LLP

(57) ABSTRACT

An endoluminal surgery system is disclosed. The endoluminal surgery system includes an operating device, a connecting rod, and a handle. The operating device includes an operating part and a connecting part. During the surgery, the operating device is placed in a body cavity through an incision, the other end of the connecting rod that is outside the body is fixedly connected with the handle. Next, the operating part is controlled through the handle outside the body to achieve the corresponding surgical operation. After the operation, cut off the connecting rod, take out the operating device from the incision, and pull out the connecting rod, leaving no wound or tiny wounds on body.

18 Claims, 17 Drawing Sheets

(52) U.S. Cl.
CPC ............ *A61B 2017/2901* (2013.01); *A61B 2017/2923* (2013.01); *A61B 2017/2944* (2013.01)

(58) Field of Classification Search
CPC .... A61B 2017/2923; A61B 2017/2944; A61B 2017/2931; A61B 2017/294; A61B 2017/2932
See application file for complete search history.

(56) References Cited

U.S. PATENT DOCUMENTS

| | | |
|---|---|---|
| 2005/0096502 A1 | 5/2005 | Khalili |
| 2008/0243106 A1 | 10/2008 | Coe et al. |
| 2010/0318107 A1 | 12/2010 | Mizrahy et al. |

FOREIGN PATENT DOCUMENTS

| | | |
|---|---|---|
| CN | 203089228 | 7/2013 |
| CN | 101530340 | 8/2013 |
| CN | 104042282 A | 9/2014 |
| CN | 104720874 A | 6/2015 |
| CN | 204542354 | 8/2015 |
| CN | 204890109 | 12/2015 |
| CN | 105291651 | 2/2016 |
| CN | 107468288 A | 12/2017 |
| CN | 206729915 | 12/2017 |
| CN | 107684448 | 2/2018 |
| CN | 108703782 | 10/2018 |
| CN | 110236613 A | 9/2019 |
| EP | 2229871 A1 | 9/2010 |
| EP | 2777562 A1 | 9/2014 |
| JP | 2004255080 | 9/2004 |
| WO | 2012040183 A1 | 3/2012 |
| WO | 2016167972 A1 | 10/2016 |
| WO | 2016168380 A1 | 10/2016 |

OTHER PUBLICATIONS

International Search Report and Written Opinion for PCT/CN2020/092118, dated Aug. 21, 2020.
Notification to Complete Formalities of Registration for Chinese Patent Application No. 201910528738.8, dated Sep. 23, 2020.
Supplementary European Search Report for European Patent Application No. EP18912007.4, dated Oct. 13, 2021.
First Office Action for Chinese Patent Application No. 201880004550.7, dated Jan. 26, 2022.

\* cited by examiner

ENDOLUMINAL SURGERY DEVICE

CROSS-REFERENCE TO RELATED APPLICATIONS

This application is a continuation-in-part application of International Application No. PCT/CN2018/080972, with the title of "Endoluminal Surgery System" filed on of Mar. 28, 2018, and further claims priority to Chinese Patent Application No. 2019105287388, with the title of "Endoluminal Surgery instrument" filed on Jun. 18, 2019, the entire contents of all of which are incorporated herein by reference.

TECHNICAL FIELD

The present invention relates to the field of surgical instruments, and particularly to an endoluminal surgery system.

BACKGROUND

Currently, endoscopic surgery is generally performed by making 3-4 incisions of 5-12 mm on the body surface through a trocar, and then extending an elongate surgical instrument into the body cavity through the trocar. If the tissues or organs need to be pulled to expose the operating site, a common method is to additionally make an incision with a trocar, insert an elongate surgery forceps, and pull the tissues or organs. When the surgery is finished, the trocar is removed and the incisions are stitched. However, the elongate surgical instrument occupies a lot of space inside the body cavity, which affects the operate of the surgeon. At the same time, the additional incision may increase the wound and pain of the patient and cause more scars on the skin of the patient. In addition, most of the endoscopic surgical instruments are integral and cannot be disassembled, so the size of the operating part in the cavity is usually limited by the size of the incision.

At present, the extreme case of the endoscopic surgery is single-incision endoscopic surgery, that is, the endoscopy, the operating part and the tissue or organ pulling instrument are inserted into the body cavity through a same incision. However, due to the limitation of the size of the single incision, when multiple surgical instruments enter the cavity through the same incision, the operation becomes inconvenient and difficult, and the risk control ability is poor when the accidents occur, which is disadvantage to popularization. Therefore, although the single-incision surgery has only one incision, the advantage of the single-incision surgery compared with multi-incision surgery is small.

BRIEF DESCRIPTION OF THE INVENTION

In view of this, the present disclosure provides an endoluminal surgery system, which can reduce the injury to the patients, and be more convenient for the surgeon to carry out the surgical operation outside the body, and improve the success rate of the endoscopic surgery.

According to one aspect of the present disclosure, there is provided an endoluminal surgery system. The endoluminal surgery system includes: an operating device including an operating part and a connecting part; a connecting rod with a piercing end configured to pierce into a body cavity; and a handle for fixing the connecting rod. The connecting part is configured to be fixedly connected with the piercing end of the connecting rod in the body cavity.

In one embodiment, the connecting part includes: a fixing groove for accommodating the piercing end of the connecting rod. The fixing groove is provided with a first limiting part for connecting the connecting rod. The piercing end of the connecting rod is provided with a second limiting part matched with the first limiting part.

In one embodiment, the connecting part further includes: a sliding groove arranged opposite to the fixing groove, a slider arranged in the sliding groove, and a transmission component. The slider and the operating part are connected. The transmission component is configured to control the movement of the slider in the sliding groove to change the working state of the operating part.

In one embodiment, the handle includes: a grip with a first channel inside, and a control device. The first channel is used for accommodating at least a portion of the transmission component. The grip is configured to be fixedly connected with the connecting rod. The control device is configured to be connected with the transmission component for controlling the movement of the transmission component.

In one embodiment, the connecting rod is provided with a hollow second channel, and the first channel is configured to be aligned with the second channel. The transmission component is a pull line in particular. One end of the pull line is configured to be fixedly connected with the slider for pulling the slider to move, and the other end of the pull line passes through the second channel and is connected with the control device.

In one embodiment, the endoluminal surgery system further includes: a hook needle with a groove or a hook arranged at the end.

In one embodiment, the connecting rod is provided with a hollow second channel, and the first channel is configured to be aligned with the second channel. The transmission component is a core rod in particular. One end of the core rod is configured to be in contact with the slider, and the other end of the core rod is in contact with the control device.

In one embodiment, the control device includes: a button for transmitting the user's force; and a transfer column arranged in the first channel. One end of the transfer column is configured to be in contact with the core rod. The transfer column is configured to move along the first channel according to the force exerted on the button so that the core rod moves along the second channel.

In one embodiment, the transfer column includes: an upper tooth column with a first tooth part; a lower tooth column with a second tooth part; and a first elastic component arranged in the first channel. The first elastic component is configured to keep the core rod and the lower tooth column in a motion trend in a first direction. The first tooth part and the second tooth part are disposed to face each other, and are configured to be engaged with each other in at least one position.

In one embodiment, the transfer column further includes: a second elastic component arranged in the first channel and in contact with the upper tooth column. The second elastic component is configured to keep the upper tooth column in a motion trend in the first direction.

In one embodiment, the connecting part further includes: a third elastic component connected with the slider for keeping the slider in a motion trend in the first direction, or for keeping the slider in a motion trend in a second direction.

In one embodiment, the connecting part further includes: a connecting piece extends along a side of the sliding groove; and the operating part is a retractor clamp in particular. The retractor clamp is connected with the connecting piece.

In one embodiment, the retractor clamp includes a first clamping arm and a second clamping arm. The first clamping arm and the second clamping arm are rotatably connected by a first hinge shaft; and the first hinge shaft is fixedly connected with the connecting piece.

In one embodiment, the first hinge shaft is provided with a fourth elastic component, the two ends of the fourth elastic component extend and are fixedly connected with the first clamping arm and the second clamping arm respectively.

In one embodiment, the first limiting part is a buckle, and the second limiting part is a clamping groove.

In one embodiment, the first limiting part and the second limiting part are threads.

In one embodiment, the first limiting part includes at least one elastic ring, and the second limiting part is provided with a clamping groove and a guide groove. The clamping groove and the guide groove are matched with the elastic ring. The connecting rod is fixed with the elastic ring by the clamping groove, and is separated from the elastic ring by the guiding groove.

In one embodiment, the first limiting part is provided with a through-hole, and a buckle is disposed in the through-hole and configured to fix the connecting rod.

The first limiting part is fixedly connected with the fixing groove by a fifth elastic component.

The second limiting part is a clamping groove. In a first state, the through-hole of the first limiting part is coaxially disposed with the fixing groove to allow the connecting rod go through the through-hole. In a second state, the buckle in the through-hole is engaged with the clamping groove to fix the connecting rod.

In one embodiment, the first limiting part is an elastic jaw; and the second limiting part is a clamping groove. The clamping groove is configured to be fixedly connected with the jaw to fix the connecting rod.

In one embodiment, the piercing end is provided a tip.

The present disclosure provides an endoluminal surgery system. The endoluminal surgery system includes: an operating device, a connecting rod, and a handle. The operating device includes an operating part and a connecting part. During the surgery, the operating device is placed in the body cavity through an incision, and the piercing end of the connecting rod enters the body cavity through a piercing point and is fixedly connected with the connecting part of the operating device. The other end, outside the body, of the connecting rod is connected with the handle. Then, the operating part can be controlled and adjusted through the handle outside the body to achieve the corresponding surgery procedures. The present disclosure can help pull the tissues or organs during operation through a tiny needle wound which need no suture after surgery. The present disclosure reduces the injury to the patient's body, makes the surgical procedures outside the body more convenient, and improves the success rate of the operation.

BRIEF DESCRIPTION OF THE DRAWINGS

The above and other objects, features, and advantages of the present disclosure will be more apparent from the following description of embodiments of the present disclosure with reference to the accompanying drawings, in which.

REFERENCE NUMERALS

Figure 1:
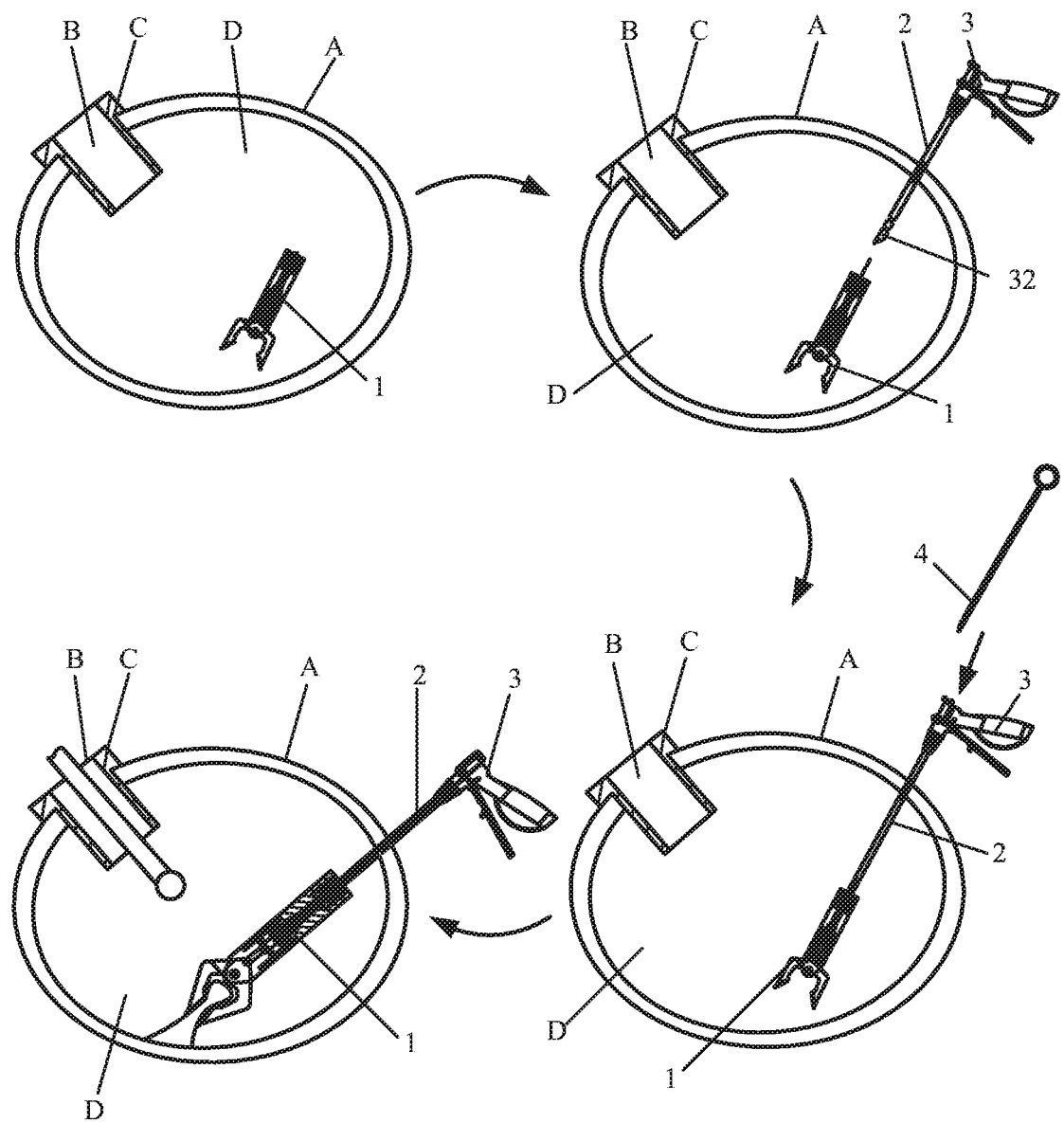
FIG. 1 is a schematic diagram illustrating operations of an endoluminal surgery system of the present disclosure.

1—operating device; 11—operating part; 111—first clamping arm; 112—second clamping arm; 113—first hinge shaft; 114—connecting arm; 115—second hinge shaft; 116—fourth elastic component; 12—connecting part; 121—fixing groove; 122—first limiting part; 122a—fifth elastic component; 122b—limiting groove; 123—sliding groove; 124—slider; 125—transmission component; 126—third elastic component; 127—connecting piece; 128—rubber protecting block; 2—connecting rod; 21—piercing end; 22—second channel; 23—second limiting part; 231—clamping groove; 232—guide groove; 3—handle; 31—grip; 311—first channel; 312—guide rail; 32—control device; 321—movable arm; 322—fixed pulleys; 323—button; 324—transfer column; 325—upper tooth column; 326—lower tooth column; 327—first elastic component; 328—second elastic component; 4—hook needle; 41—groove; 42—hook; A—body surface; B—incision; C—trocar; D—body cavity; E—elongate surgical instrument; F—organ or tissue in cavity.

DETAILED DESCRIPTION

The present disclosure is described below based on embodiments, but the present disclosure is not limited to these embodiments. In the following detailed description of the present disclosure, some specific details are described in detail. To those skilled in the art, the present invention can be fully understood without the description of these details. In order to avoid obscuring the essence of the present disclosure, well-known methods, procedures, processes, components, and circuits have not been described in detail.

In addition, it will be understood by those skilled in the art that the drawings provided herein are for illustrative purpose and are not necessarily drawn to scale.

Unless the context clearly requires otherwise, the words "comprising", "including" and the like in the entire specification and claims should be construed as the meaning of inclusion rather than the meaning of exclusion or exhaustion, that is, the meaning of "including but not limited to".

In the description of the present disclosure, it should be understood that the terms "first", "second" and the like are for illustrative purposes only and should not to be construed as indicating or implying relative importance. In addition, in the description of the present disclosure, the meaning of "a plurality of" means two or more, unless otherwise specified.

Unless otherwise expressly specified or defined, terms "mount", "couple", "connect" and "fix" should be understood in a broad sense, and for example, a connection may be a fixed connection, or a detachable connection, or an integrated connection; a connection may be a mechanical connection or an electric connection; a connection may be a direct connection, or an indirect connection via an intermediate medium, or may be an internal communication between two elements or an interaction between two elements. Unless otherwise expressly specified, the specific meanings of the above-mentioned terms as used herein could be understood by those skilled in the art according to specific situations.

When an element or layer is referred to as being "on", "joined to", "connected to" or "coupled to" another element or layer, it may be directly on, joined, connected or coupled to the other element or layer, or intervening elements or layers may be present. In contrast, when an element is referred to as being "directly on", "directly joined to", "directly connected to" or "directly coupled to" another element or layer, there may be no intervening elements or layers present. Other words used to describe the relationship between elements should be interpreted in a like fashion (e.g., "between" versus "directly between", "adjacent" versus "directly adjacent", etc.). As used herein, the term "and/or" includes any and all combinations of one or more of the associated listed items.

For ease of explanation, spatially relative terms, such as "inner", "outer", "beneath", "below", "lower", "above", "upper" and the like, may be used herein to describe one element or feature's relationship to another element(s) or feature(s) as illustrated in the figures. It will be understood that spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated by 90 degrees or at other orientations) and the spatially relative descriptors used herein interpreted accordingly.

FIG. 1 is a schematic diagram illustrating operations of an endoluminal surgery system of the present disclosure. Referring to FIG. 1, the endoluminal surgery system includes an operating device 1, a connecting rod 2 and a handle 3. The handle 3 is used for fixing the connecting rod 2, and the connecting rod 2 may include a piercing end 21 configured to pierce into a body cavity D. The operating device 1 may include an operating part 11 and a connecting part 12. The connecting part 12 is configured to be fixedly connected with the piercing end 21 of the connecting rod 2 in the body cavity D. The connecting rod 2 may be a solid needle or a hollow needle. If the connecting part 12 is provided with a transmission component 125, the connecting rod 2 is a hollow needle. During the surgery, the surgeon makes an incision B on the patient's body surface A according to needs, and then inserts a trocar C corresponding to the size of the incision B for forming a passage for entry or exit of the surgical instruments. The surgeon places the operating device 1 through the trocar C into the body cavity D. The surgeon holds the handle 3 and pierces the piercing end 21 of the connecting rod 2 into the patient's body cavity D through another position on the patient's body surface A. The surgeon can use an elongate surgical instrument through the incision B to fixedly connect the piercing end 21 and the operating device 1 in the body cavity D. Then, the surgeon can control the operating device 1 through the handle 3 outside the body and perform the corresponding operation on the tissue or organ. If necessary, multiple operating devices 1 can be placed in the body cavity D to operate different parts of the tissue or organ so as to better expose the operation part. The endoluminal surgery system of the embodiments of present disclosure can help avoid the mutual interference between multiple surgical instruments which enter the body cavity through the same incision during surgery, where the mutual interference affects the flexibility of surgical operation, and also can reduce the injury to the patients.

First Embodiment

Figure 2:
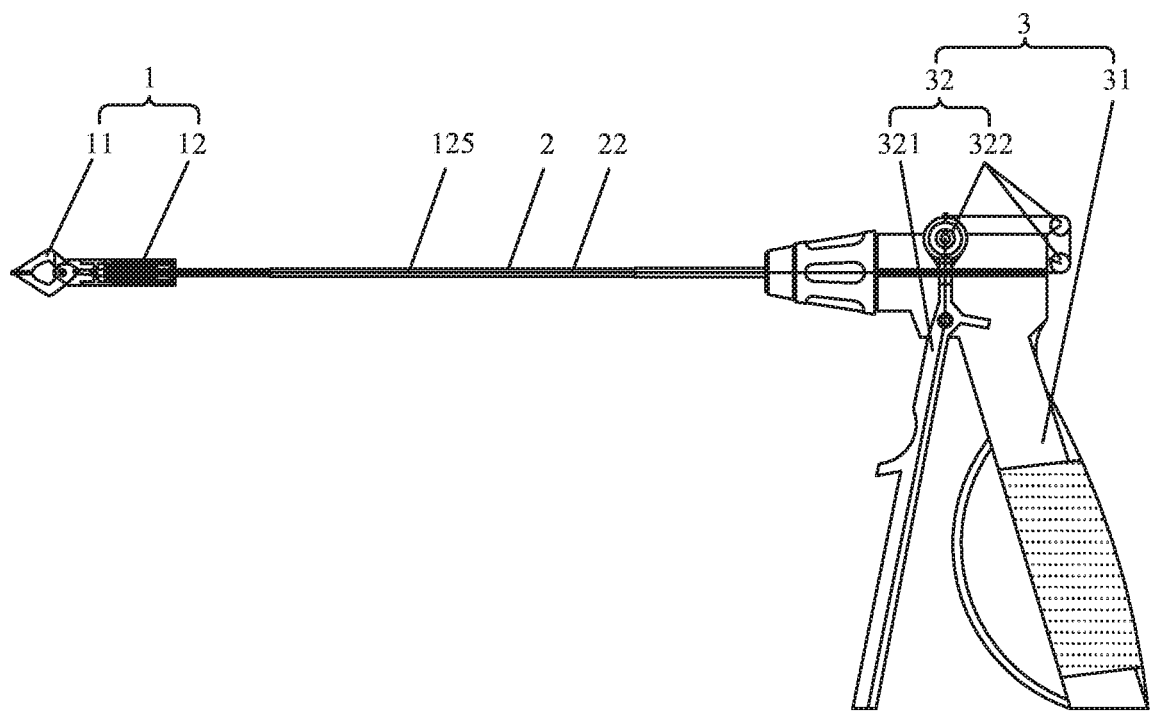
FIG. 2 is a schematic diagram of an endoluminal surgery system according to the first embodiment of the present disclosure.

FIG. 2 is a schematic diagram of the endoluminal surgery system according to the first embodiment of the present disclosure. As shown in FIG. 2, the endoluminal surgery system includes an operating device 1, a connecting rod 2 and a handle 3. In this embodiment of the present disclosure, the endoluminal surgery system is provided with a pull line 125, and the connecting rod 2 is a hollow needle. The operating device 1 is configured to be disposed in a thoracic or abdominal cavity for performing the corresponding operation on a lesion of the patient.

FIG. 3 to FIG. 7 are schematic diagrams illustrating the connecting part 12. Referring to FIG. 3 to FIG. 7, in the present embodiment, the operating device 1 includes an operating part 11 and a connecting part 12. The operating part 11 may be a pull forceps, a pair of medical scissors or other surgical instrument suitable for an endoscopic surgery. The connecting part 12 includes a fixing groove 121, a sliding groove 123, a slider 124 and a transmission component 125. In this embodiment of the present disclosure, the transmission component 125 is a pull line 125. A first limiting part 122 for fixing the connecting rod 2 is arranged in the fixing groove 121. In the present embodiment, the connecting rod 2 is a hollow needle 2 with a second channel 22, and a piercing end 21 of the hollow needle 2 is provided with a second limiting part 23 which is matched with the first limiting part 122. When the piercing end 21 of the hollow needle 2 enters the fixing groove 121, the hollow needle 2 and the connecting part 12 are fixedly connected through the first limiting part 122 and the second limiting part 23. The connecting part 12 can be made of materials with high strength and hardness such as alloy steel, which can improve the strength of the operating device 1, and can also be used for making small size structures to meet usage requirements.

Figure 3:
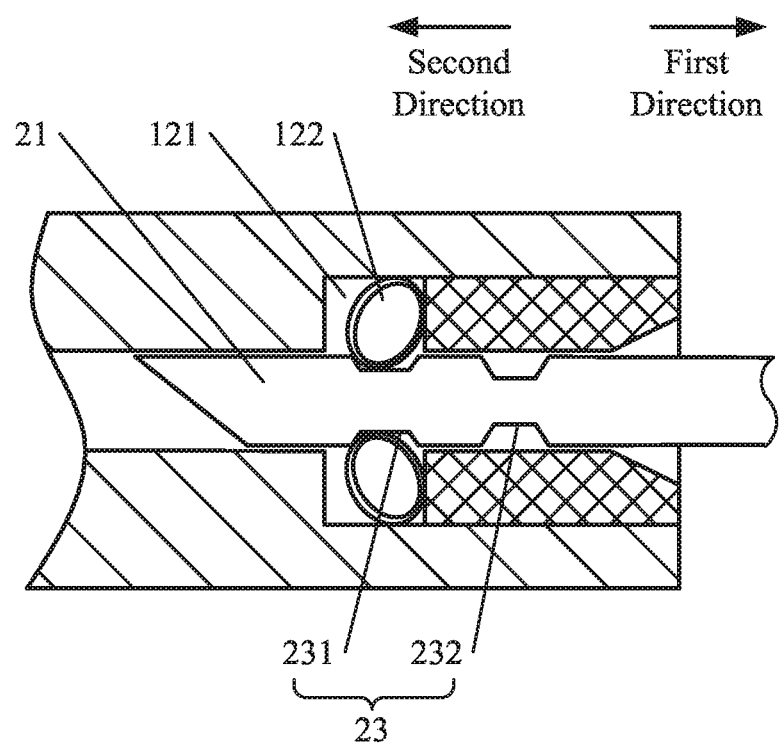
FIG. 3 is a first schematic diagram of a connecting part according to the first embodiment of the present disclosure.

As shown in FIG. 3, in an optional implementation, the first limiting part 122 may include at least one elastic ring, which is embedded in the fixing groove 121. The inner diameter of the elastic ring in the natural state is smaller than the outer diameter of the hollow needle 2, where the natural state refers to the state in which the elastic ring is not subjected to any external force. The second limiting part 23 may include a clamping groove 231 and a guide groove 232. The clamping groove 231 and the guide groove 232 are matched with the elastic ring. The clamping groove 231 and the guide groove 232 may be placed successively from the piercing end 21 of the hollow needle 2 to a fixed end of the connecting rod 2. The clamping groove 231 is smaller than the guide groove 232. When the piercing end 21 of the hollow needle 2 enters the clamping groove 231, the elastic ring is pressed into the clamping groove 231. Due to the small accommodation space of the clamping groove 231, the elastic ring is deformed, and the cross section of the elastic ring becomes approximately elliptic. The major axis of the elliptic forms an acute angle with the insertion direction of the hollow needle 2. At this time, at the contact point between the clamping groove 231 and the elastic ring, the pulling-out direction of the hollow needle 2 is the same as the rotation direction of the major axis of the elliptic, so a resistance is relatively large, and it is difficult to pull out the hollow needle 2. When it needs to separate the hollow needle 2 from the connecting part 12, the surgeon may insert the hollow needle 2 into the fixing groove 121 further. Since the insertion direction of the hollow needle 2 is the same as the rotation direction of the major axis of the elliptic, the resistance is relatively small, and the elastic ring can enter the guide groove 232 easily. Because the space of the guide groove 232 is larger, the elastic ring returns to its natural state. Then, the hollow needle 2 is pulled out, the elastic ring is inserted into the clamping groove 231 and deformed again, and the cross section of the elastic ring becomes approximately elliptic again. The major axis of the elliptic forms an obtuse angle with the pulling direction of the hollow needle 2. At this time, at the contact point between the clamping groove 231 and the elastic ring, the pulling direction of the hollow needle 2 is the same as the rotation direction of the major axis of the elliptic so that the obtuse angle becomes larger. Since the resistance is relatively small, it is easy to pull out the hollow needle 2 from the fixing groove 121 to realize the separation. Undoubtedly, the surgeon can also cut off the hollow needle 2 to separate the hollow needle 2 from the operating device 1.

Figure 4:
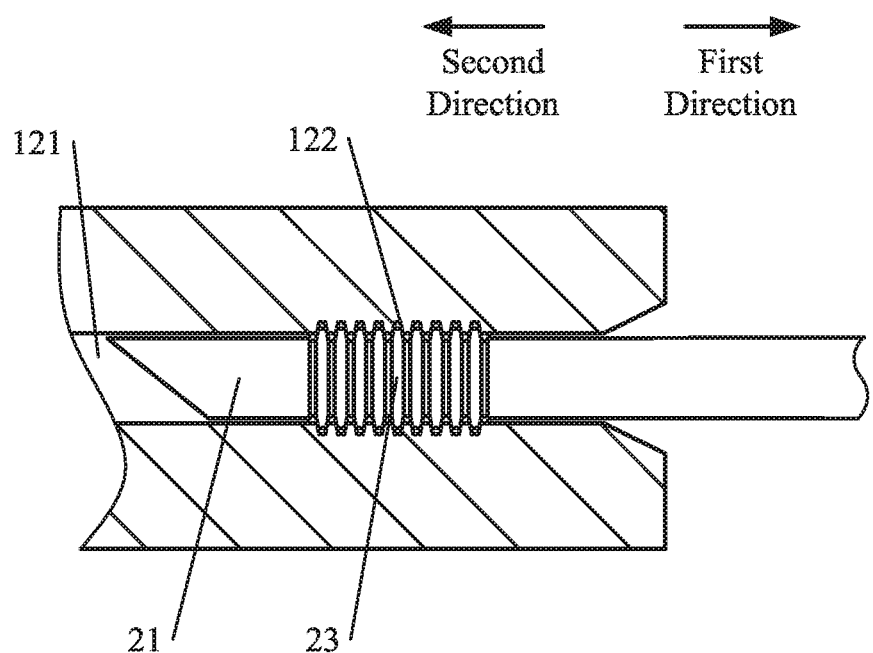
FIG. 4 is a second schematic diagram of a connecting part according to the first embodiment of the present disclosure.

As shown in FIG. 4, in another implementation, the first limiting part 122 may be set to an internal thread and the second limiting part 23 may be set to an external thread matched with the internal thread. The hollow needle 2 can be fixedly connected to the connecting part 12 by the threads.

Figure 5:
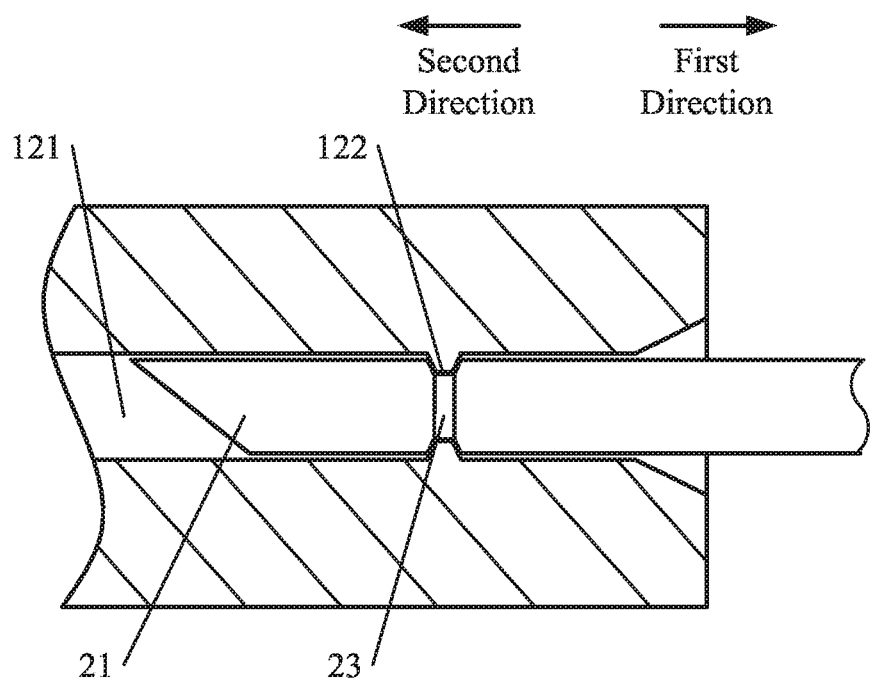
FIG. 5 is a third schematic diagram of a connecting part according to the first embodiment of the present disclosure.

As shown in FIG. 5, in another implementation, the first limiting part 122 may be set to an elastic buckle and the second limiting part 23 of the hollow needle 2 may be set to a clamping groove matched with the elastic buckle. After the hollow needle 2 enters the body cavity through the piercing point, the hollow needle 2 and the connecting part 12 can be fixedly connected through the elastic buckle and the clamping groove. The surgeon can cut off the hollow needle 2 to separate the hollow needle 2 from the operating device 1.

Figure 6:
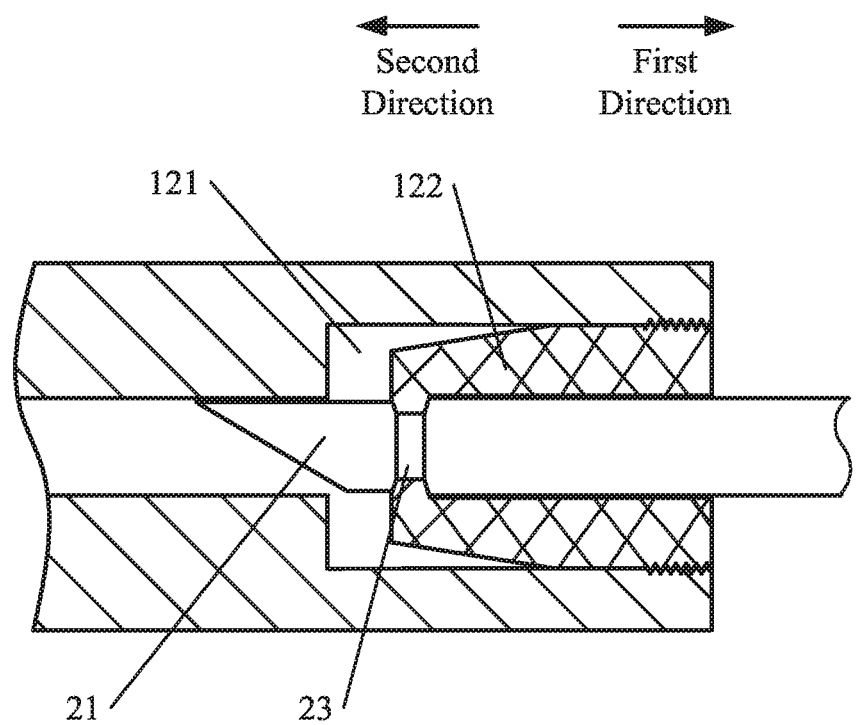
FIG. 6 is a fourth schematic diagram of a connecting part according to the first embodiment of the present disclosure.

As shown in FIG. 6, in another implementation, the first limiting part 122 may be set to an elastic jaw, which is in the fixing groove 121 and fixed to the end of the fixing groove 121. The elastic jaw is provided with protrusions, and the second limiting part 23 may be clamping grooves matched with the protrusions. When the hollow needle 2 enters the body cavity through the piercing point, the elastic jaw moves along the piercing end 21 based on its elasticity. When reaching the grooves, the accommodating space becomes larger, so the protrusions of elastic jaw return to the natural state (the state in which they are not subjected to any external force), and the protrusions of elastic jaw are fixedly connected with the clamping grooves.

Figure 7:
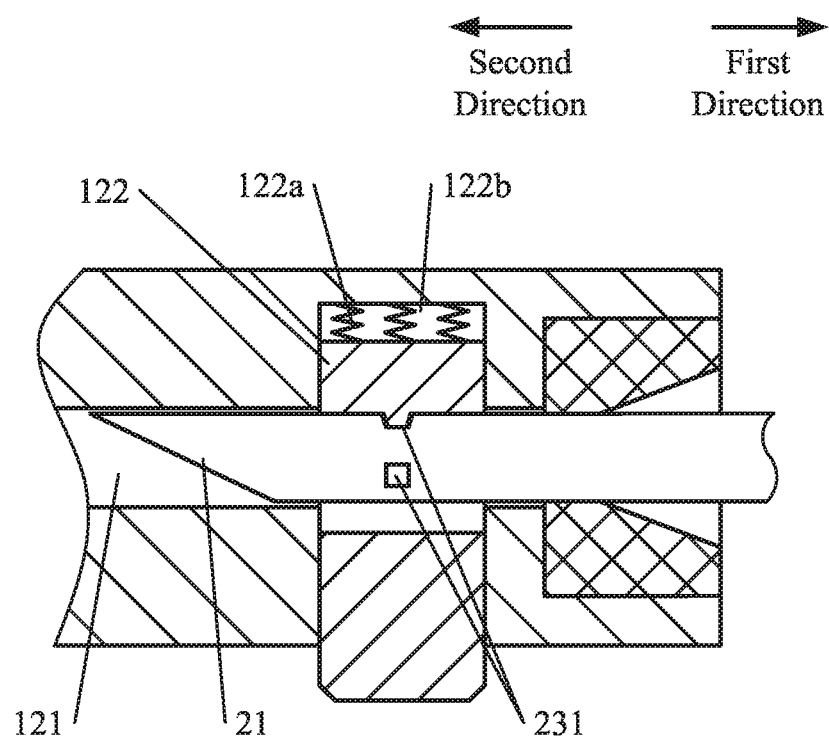
FIG. 7 is a fifth schematic diagram of a connecting part according to the first embodiment of the present disclosure.

As shown in FIG. 7, in another implementation, the first limiting part 122 may be set to a movable buckle 122. One end of the movable buckle 122 runs through the connecting part 12 and is outside the connecting part 12, and the other end may be fixedly connected with the fixing groove 121 through a fifth elastic component 122a. The fixing groove 121 is provided with a limiting groove 122b in a longitudinal direction, which is used for accommodating the movable buckle 122. The movable buckle 122 is able to move in the limiting groove 122b because of the elasticity of the fifth elastic component 122a. The movable buckle 122 may be provided with a through-hole, and at least one fixing buckle is disposed in the through-hole for fixing the hollow needle 2. The second limiting part 23 may be the clamping groove 231. Optionally, three second limiting parts 23, that is, three clamping grooves 231, are evenly disposed on the hollow needle 2 in the circumferential direction of the hollow needle 2 so that the hollow needle 2 can be fixedly connected with the connecting part 12 at three positions. It will be understood by those skilled in the art that the number of the clamping groove 231 could be set to other number as required.

Figures 8A, 8B:
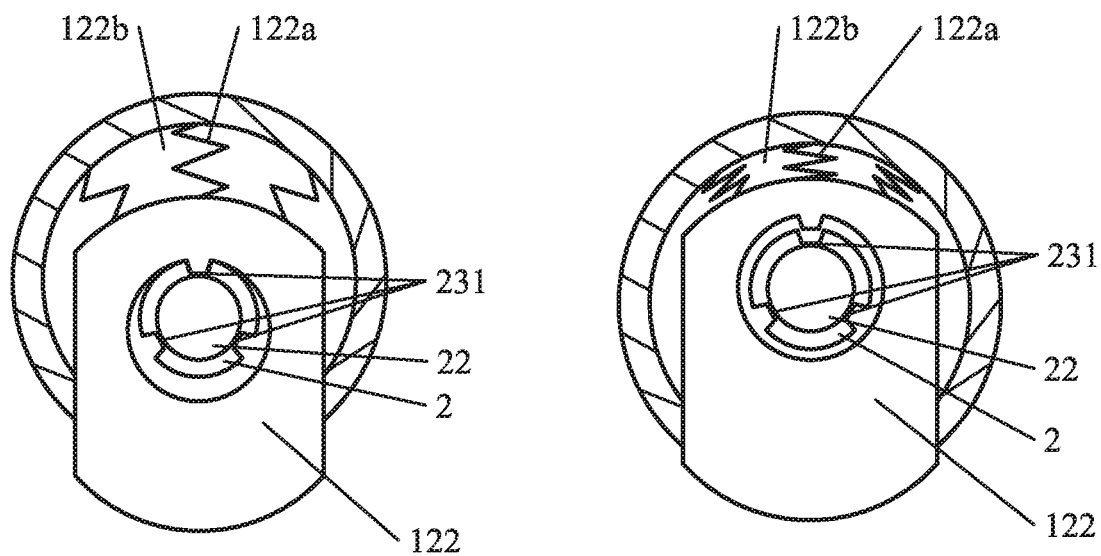
FIG. 8A is a schematic diagram of a first limiting part of the connecting part in the first embodiment of the present disclosure shown in FIG. 5 in a first state.
FIG. 8B is a schematic diagram of the first limiting part of the connecting part in the first embodiment of the present disclosure shown in FIG. 5 in a second state.

FIG. 8A and FIG. 8B are schematic diagrams illustrating the first limiting part 122 of the connecting part 12 of FIG. 7 in a first state and a second state respectively. As shown in FIG. 8A and FIG. 8B, in the first state, the fixing buckle in the through-hole is connected with the clamping grooves 231 and mates with the clamping grooves 231 to fix the hollow needle 2. In the second state, the through-hole of the first limiting part 122 is coaxial with the fixing groove 121 so that the hollow needle 2 can pass through the through-hole. When the first limiting part 122 in the fixing groove 121 is in the first state, as shown in FIG. 8A, the distance between the center axis of the through-hole of the first limiting part 122 and the center axis of the fixing groove 121 is large so that the hollow needle 2 cannot pass through the through-hole. When the first limiting part 122 in the fixing groove 121 is in the second state, as shown in FIG. 8B, the center axis of the through-hole of the first limiting part 122 coincides or approximately coincides with the center axis of the fixing groove 121 so that the hollow needle 2 can pass through the through-hole. When the hollow needle 2 needs to be connected with the operating device 1, the surgeon can use a surgical instrument such as forceps to press the first limiting part 122, that is, the moveable buckle, from the outside of the operating device 1 so that the connecting rod 2 passes through the through-hole of the first limiting part 122, and the clamping groove 231 of the connecting rod 2 is aligned with the fixing buckle of the through-hole of the first limiting part 122. Next, the first limiting part 122 is released to clamp the hollow needle 2. When it needs to pull out the hollow needle 2, he can use the surgical forceps to press the first limiting part 122 from the outside of the operating device 1 again, so that the hollow needle 2 can pass through the through-hole of the first limiting part 122 and be separated from the operating device 1.

FIG. 9A to FIG. 11B are schematic diagrams illustrating states of the operating device 1 according to the first embodiment of the present disclosure. As shown in FIG. 9A to FIG. 11B, in the present embodiment, the connecting part 12 may further include a sliding groove 123, a slider 124 and a transmission component 125. The sliding groove 123 may be arranged on the side of the connecting part 12 opposite to the fixing groove 121, and the slider 124 may be placed in the sliding groove 123. One end of the slider 124 is connected with the operating part 11, and the operating part 11 is driven by the movement of the slider 124 in the sliding groove 123. In the present embodiment, the transmission component 125 is a pull line, and the other end of the slider 24 is detachably connected with the pull line 125. The pull line 125 can drive the slider 124 to move along the sliding groove 123, so that the slider 124 drives the operating part 11. After the hollow needle 2 enters the body cavity through the piercing point and is fixedly connected with the operating device 1, the surgeon causes the pull line 125 to pass through the hollow needle 2 and then control the operating part 11 by controlling the pull line 125 outside the body cavity of the patient.

As shown in FIG. 9A to FIG. 11B, in the present embodiment, the operating part 11 is a retractor clamp 11, such as a lung clamp, a stomach clamp, an intestinal clamp, a liver clamp, a tendon clamp, a vascular clamp, and the like. The surgeon can choose a specific retractor clamp according to the target tissues or organs. The retractor clamp 11 may include a first clamping arm 111 and a second clamping arm 112. The first clamping arm 111 and the second clamping arm 112 may be rotatably connected through a first hinge shaft 113. The retractor clamp 11 may be also connected with the connecting part 12 through the first hinge shaft 113. The inner surface of the first clamping arm 111 and the inner surface of the second clamping arm 112 may be provided with antiskid strips to prevent the tissues or organs from slipping out of the retractor clamp 11 when the retractor clamp 11 is in the close state. Each of the tail of the first clamping arm 111 and the tail of the second clamping arm 112 is provided with a mounting hole. One of the two mounting holes is connected to an end of one of two connecting arms 114, and the other one of the two mounting holes is connected to an end of the other one of the two connecting arms 114. The other ends of the two connecting arms 114 are rotatably connected through a second hinge shaft 115. The slider 124 is connected with the second hinge shaft 115 or the two connecting arms 114.

The connecting part 12 may further include at least one connecting piece 127, which is arranged on the side of the connecting part 12 opposite to the sliding groove 123 and extends along the sliding groove 123. The connecting part 12 is provided with a connecting hole. The first hinge shaft 113 may pass through the connecting hole and connect the retractor clamp 11 with the connecting part 12.

As shown in FIG. 9A to FIG. 10B, in an optional implementation, in the natural state (no external force is applied), an included angle between the two connecting arms 114 is large, and the retractor clamp 11 is opened. When the pull line 125 pulls the slider 124 in the first direction, the included angle between the two connecting arms 114 decreases gradually, which drives the first clamping arm 111 and the second clamping arm 112 to rotate relatively and clamp the target tissue or organ. Then the surgeon can move the target tissue or organ as needed to provide a good surgical field of view.

To easily open the retractor clamp 11 after the operation is complete, the operating part 11 further includes some components that assist in resetting the first clamp arm 111 and the second clamp arm 112.

Figure 9A:
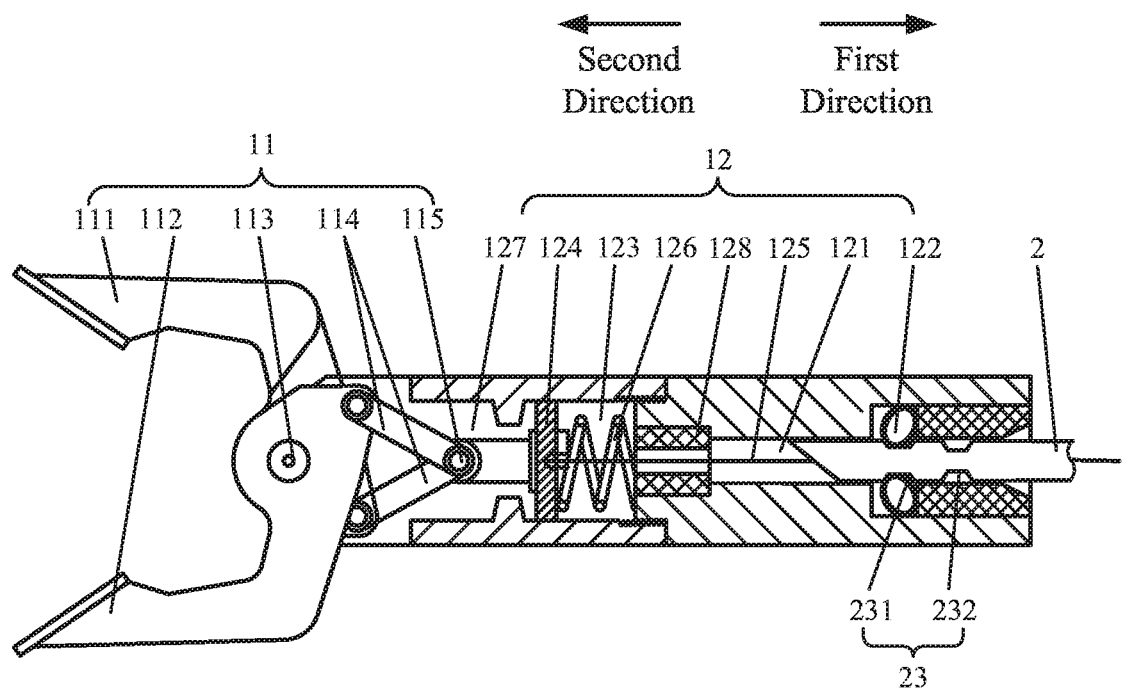
FIG. 9A is a schematic diagram of a first type operating device in an open state according to the first embodiment of the present disclosure.
Figure 9B:
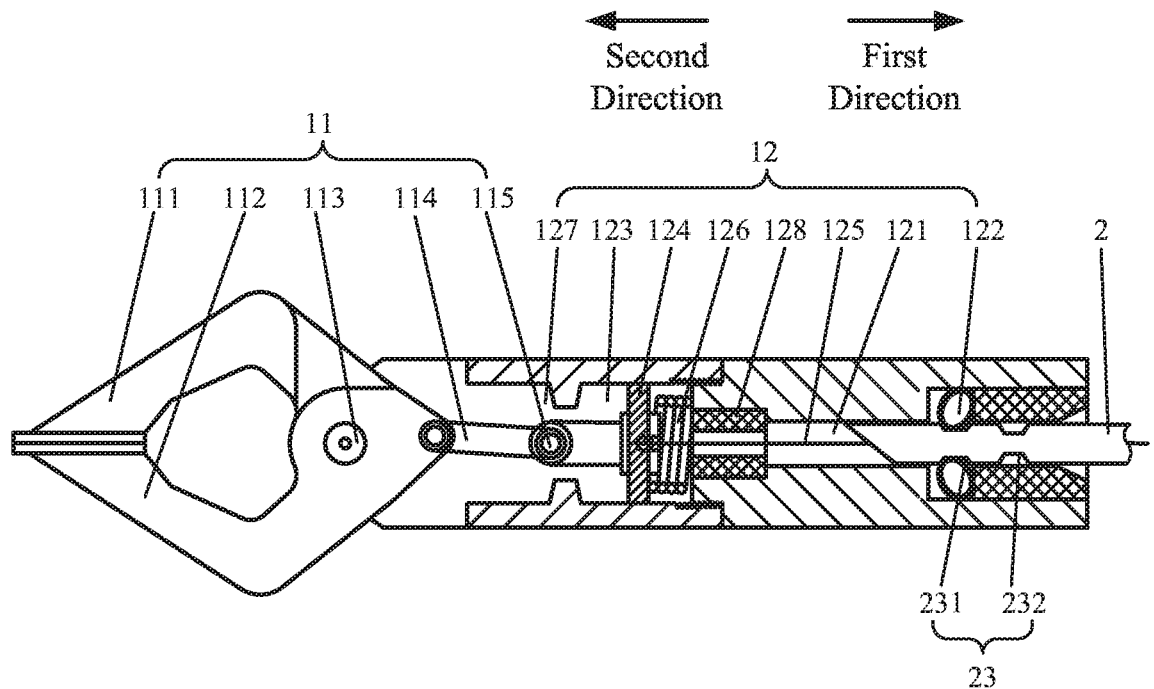
FIG. 9B is a schematic diagram of the first type operating device in a close state according to the first embodiment of the present disclosure.

As shown in FIG. 9A to FIG. 9B, in an optional implementation, a lug boss may be arranged at the end of the sliding groove 123 near the fixing groove 121, and a third elastic component 126 may be arranged in the space between the lug boss and the slider 124. When the pull line 125 is pulled in the first direction to move the slider 124, the third elastic component 126 is compressed. When the pull line 125 is released, the slider 124 moves in the second direction under the action of the elasticity of the third elastic component 126, which drives the first clamping arm 111 and the second clamping arm 112 to rotate relatively so that the retractor clamp 11 will return to the natural state.

Figure 10A:
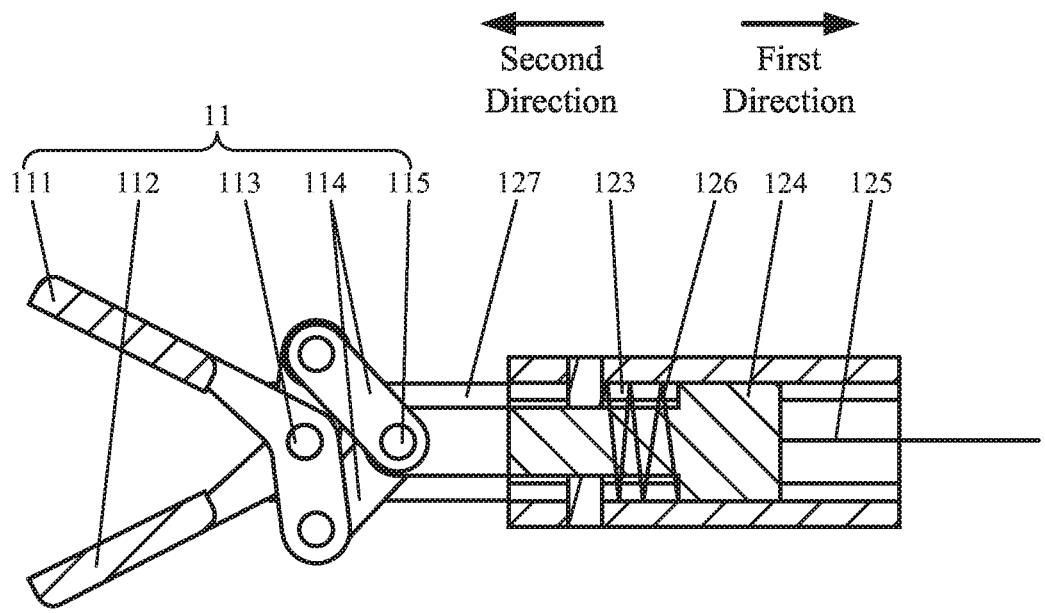
FIG. 10A is a schematic diagram of a second type operating device in an open state according to the first embodiment of the present disclosure.
Figure 10B:
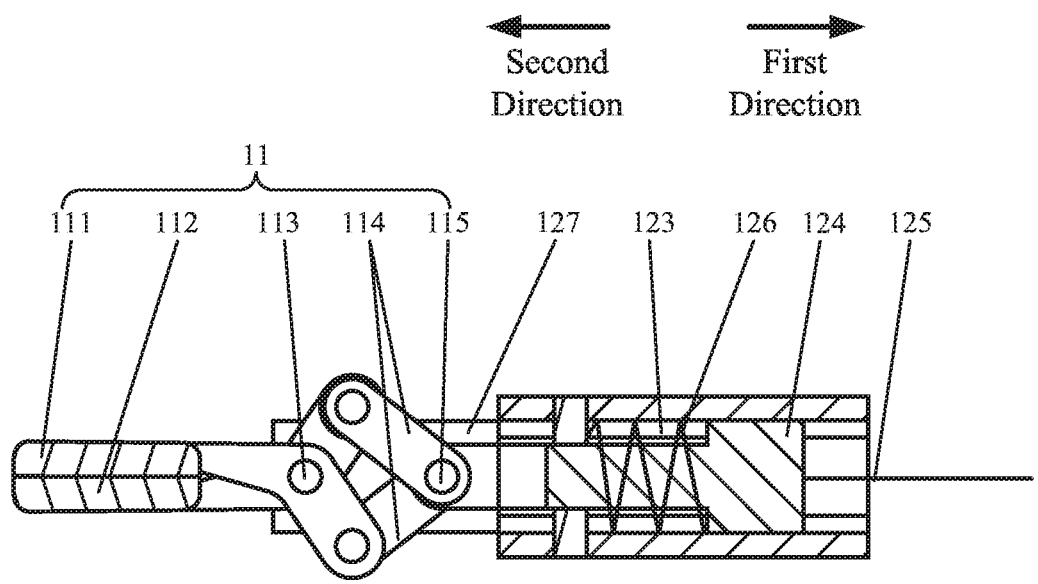
FIG. 10B is a schematic diagram of the second type operating device in a close state according to the first embodiment of the present disclosure.

As shown in FIG. 10A to FIG. 10B, in another implementation, a lug boss may be arranged at the end of the sliding groove 123 away from the fixing groove 121. The third elastic component 126 is arranged between the lug boss and the slider 124. Two ends of the third elastic component 126 are fixedly connected with the lug boss and the slider 124 respectively. When the pull line 125 is pulled in the first direction, the third elastic component 126 is stretched. When the pull line 125 is released, the slider 124 may be moved in the second direction under the action of the elasticity of the third elastic component 126, driving the first clamping arm 111 and the second clamping arm 112 to rotate relatively so that the retractor clamp 11 will return to the natural state.

Figure 11A:
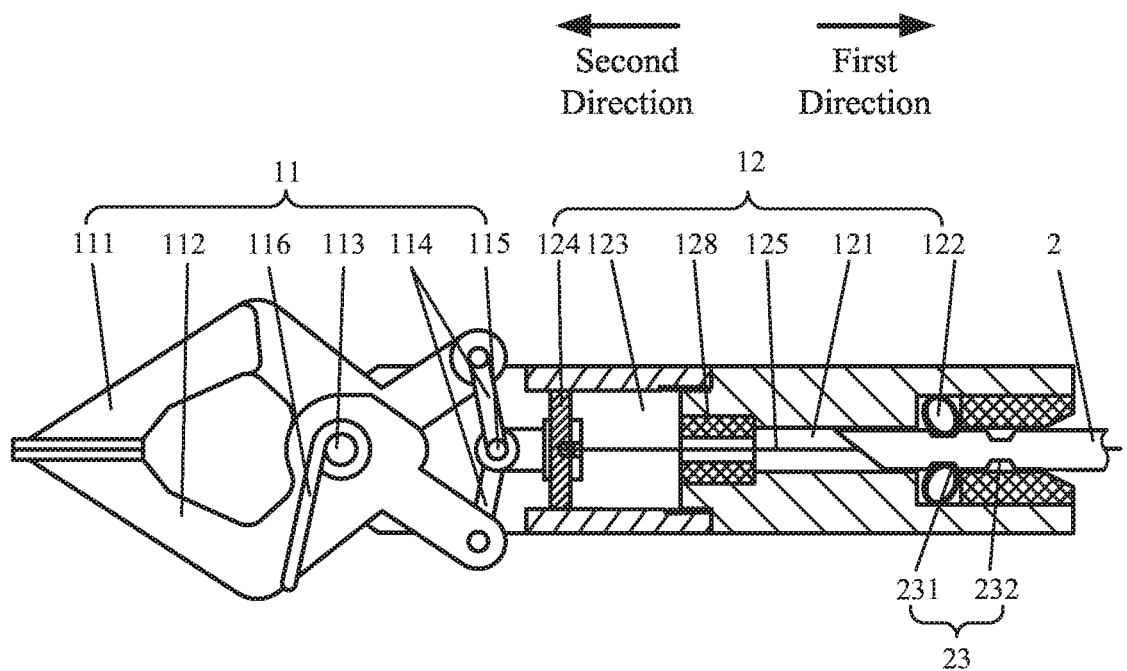
FIG. 11A is a schematic diagram of a third type operating device in a close state according to the first embodiment of the present disclosure.
Figure 11B:
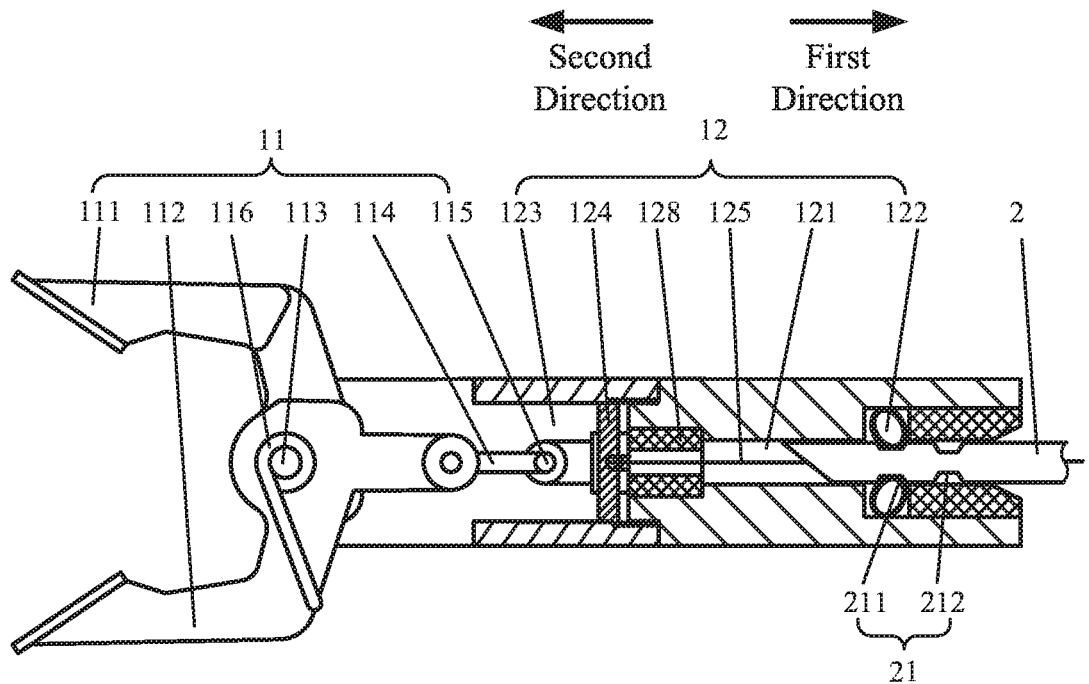
FIG. 11B is a schematic diagram of the third type operating device in an open state according to the first embodiment of the present disclosure.

As shown in FIG. 11A to FIG. 11B, in another implementation, the operating instruction 11 is a retractor clamp with a fourth elastic component 116, and the third elastic component 126 may be not provided in the connecting part 12 according to needs. The retractor clamp 11 may include a first clamping arm 111 and a second clamping arm 112. The first clamping arm 111 and the second clamping arm 112 may be rotatably connected through a first hinge shaft 113. The fourth elastic component 116 is disposed on the first hinge shaft 113. Two ends of the fourth elastic component 116 extend and are fixedly connected with the first clamping arm 111 and the second clamping arm 112 respectively. Further, the retractor clamp 11 may be also connected with the connecting part 12 through the first hinge shaft 113. The inner surface of the first clamping arm 111 and the inner surface of the second clamping arm 112 may be provided with antiskid strips to prevent the tissues or organs from slipping during the closing of the first and second clamping arms. Each of the tail of the first clamping arm 111 and the tail of the second clamping arm 112 is provided with a mounting hole. One of the two mounting holes is connected to an end of one of two connecting arms 114, and the other one of the two mounting holes is connected to an end of the other one of the two connecting arms 114. The other ends of the two connecting arms 114 are rotatably connected through a second hinge shaft 115. The slider 124 is connected with the second hinge shaft 115 or the two connecting arms 114. In the natural state, an included angle between the two connecting arms 114 is large, and the retractor clamp is in a close state. When the slider 124 is pulled by the pull line 125 and moves to the fixing groove 121, the angle between the two connecting arms 114 decreases gradually, which drives the first clamping arm 111 and the second clamping arm 112 to rotate relatively, and the retractor clamp 11 is in the open state. The retractor clamp 11 is moved to the target tissue or organ, the pull line is released, and the retractor clamp returns to the natural state and is in the close state because of the elasticity of the fourth elastic component 116 so that the target tissue or organ is clamped. The clamped target tissue or organ is moved as needed to provide a good surgical field of view.

Figure 12:
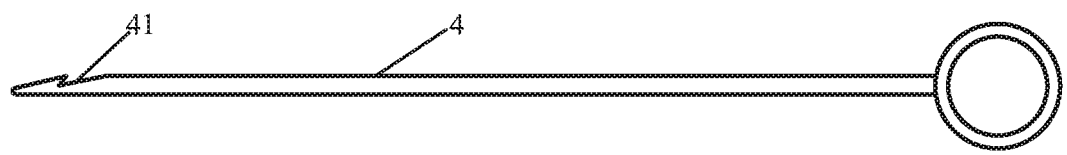
FIG. 12 is a first schematic diagram of a hook needle according to the first embodiment of the present disclosure.
Figure 13:
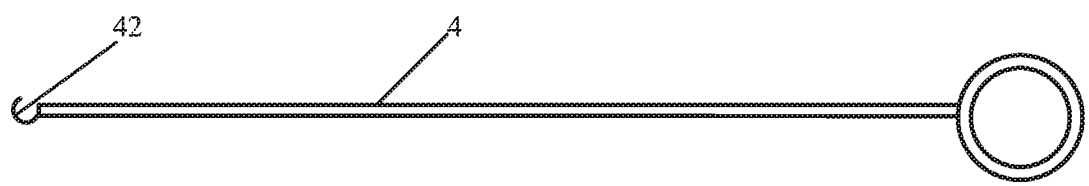
FIG. 13 is a second schematic diagram of the hook needle according to the first embodiment of the present disclosure.

As shown in FIG. 12 and FIG. 13, the endoluminal surgery system further includes a hook needle 4. The hook needle 4 includes a groove 41 or a hook 42 disposed at an end of the hook needle 4. As shown in FIG. 12 and FIG. 13, the diameter of the hook needle 4 is smaller than the inner diameter of the hollow needle 2. After the hollow needle 2 passes through the body surface A and enters the body cavity D, the hook needle 4 is sent from outside into the body cavity D through the hollow needle 2. The pull line 125 is placed with the groove 41 or the hook 42 of the hook needle 4 and extends out of the hollow needle 2. Then, the hollow needle 2 is fixedly connected with the operating device 1 and the pull line 125 is connected with the handle 3, so that the pull line 125 is controlled through the handle 3 to move, and the operating part 11 is pulled accordingly.

Optionally, if it does not need to operate the operating part 11 temporarily during the surgery, the surgeon may use handle 3 and the hollow needle 2 from outside to pull the operating device 1 to a position convenient for the surgery, and a vascular forceps or other surgical instrument can be used for fixation, so as not to cause an adverse effects for the surgery.

In the surgery, if the outer diameter of the hollow needle 2 is less than 3 mm, the hollow needle 2 enters the cavity through the piercing point. After the hollow needle 2 is pulled out, because of the self-contracting function of muscles and skins, the piercing point caused by the hollow needle 2 may recover on its own and may no need to be sutured. The wound on the body surface is reduced by using the non-invasive manner. In the present embodiment, the hollow needle 2 includes a piercing end 21 and a fixed end. Optionally, the outer diameter of the piercing end 21 of the hollow needle 2 may be set to 2.5 mm, 2 mm, or 1.5 mm to meet different operation requirements and be convenient for manufacturing. Of cause, those skilled in the art can design the diameter of the connecting rod 2 according to needs. The piercing end 21 is configured to puncture into the body cavity and fixedly connect with the operating device 1, its outer diameter is 2 mm, its inner diameter is 0.8 mm, and its length is about 100 mm. The fixed end is configured to be connected with the handle 3, and has an outer diameter of about 10 mm and a length of about 100 mm. Thus, the length of the most elongate part of the hollow needle 2 can be minimized, which enables the hollow needle 2 to withstand greater force and reduces the vibration of the piercing end 21.

Preferably, the middle part of the piercing end 21 is provided with a frosted surface. The middle part of the piercing end 21 may include several parts in the longitudinal direction, each of which has a predetermined length and is provided with a frosted surface. Alternatively, the middle part is a frosted rod between the piercing end 21 and the fixed end, the frosted rod has a predetermined length, and two ends of the frosted rod are connected to the piercing end 21 and the fixed end respectively. The predetermined length may be to 10 mm, or the predetermined length can be designed according to different surgeries or different patients. In order to prevent the piercing end 21 of the hollow needle 2 from being damaged by the high strength and high hardness connecting part 12 after the hollow needle 2 enters the fixing groove 121, a rubber protecting block 128 may be arranged at the end of the fixing groove 121 to protect the piercing end 21 of the hollow needle 2. The rubber block 128 is provided with a hole to facilitate the pull line 125 to pass through. After the operation is finished, the hollow needle 2 is pulled out from the body of the patient, there is no scar at the piercing point, and no suturing is needed, so the non-invasive operation is achieved and the operation convenience is improved.

The handle 3 includes a grip 31 and a control device 32. The grip 31 is provided with a first channel 311, and is further provided with a mounting hole for fixing the fixed end of the hollow needle 2. The control device 32 may include a movable arm 321 and fixed pulleys 322. The pull line 125 enters the second channel 22 of the hollow needle 2 through the piercing end 21 of the hollow needle 2, passes through the first channel 311 of the grip 31 and extends out the first channel 311 of the grip 31, the pull line 125 is twined around the fixed pulleys 322 in a predetermined direction and connected with a top end of the movable arm 321. Thus, the surgeon can control the pull line 125 to move within the second channel 22 of the hollow needle 2 by clenching or loosening the movable arm 321, which drives the retractor clamp to open and or close and realizes the purpose of controlling the operating device 1 with the handle 3.

During the operation, the surgeon needs to cut an incision B on the patient's body surface A, and then inserts a trocar C corresponding to the size of the incision B to the incision B to form a passage for entry or exit of the surgical instruments. Then, the surgeon places the operating device 1 through the trocar C into the body cavity D. The surgeon makes the handle 3 and the hollow needle 2 fixedly connected, and pierces the piercing end 21 into the patient's body cavity D through a selected piercing point on the patient's body surface A. The hollow needle 2 is fixedly connected with the connecting part 12 of the operating device 1, the hook needle 4 enters the cavity through the hollow needle 2, and the pull line 125 is pulled out of the body cavity D by the hook needle 4 and is fixedly connected with the handle 3. By clenching or loosening the movable arm 321, the surgeon can control the pull line 125 to move in the connecting part 12, and thus can control the retractor clamp 11 to clamp the organ that needs to be exposed. If necessary, multiple operating devices 1 can be placed in the body cavity D so that different parts of the target tissue can be clamped for better exposing the target tissue. At the end of the surgery, the retractor clamp 11 is opened by adjusting the length of the pull line 125, and then the pull line 125 is disconnected from the handle 3, so that the hollow needle 2 is separated from the connecting part 12 of the operating device 1. The hollow needle 2 is pulled out from the body, and the operating devices 1 can be taken out of the body cavity D through the trocar C. At last, the incision is sutured to finish the operation. In another implementation, the hollow needle 2 is directly cut off, and then the operating device 1 and the hollow needle 2 in the cavity are taken out of the body though the incision. The endoluminal surgery system of the present embodiment is a non-invasive surgery system and can reduce the injury to the body of the patient. Furthermore, with the endoluminal surgery system of the present embodiment, the pull force and pull direction can be more conveniently adjusted outside the body.

Second Embodiment

Figure 14:
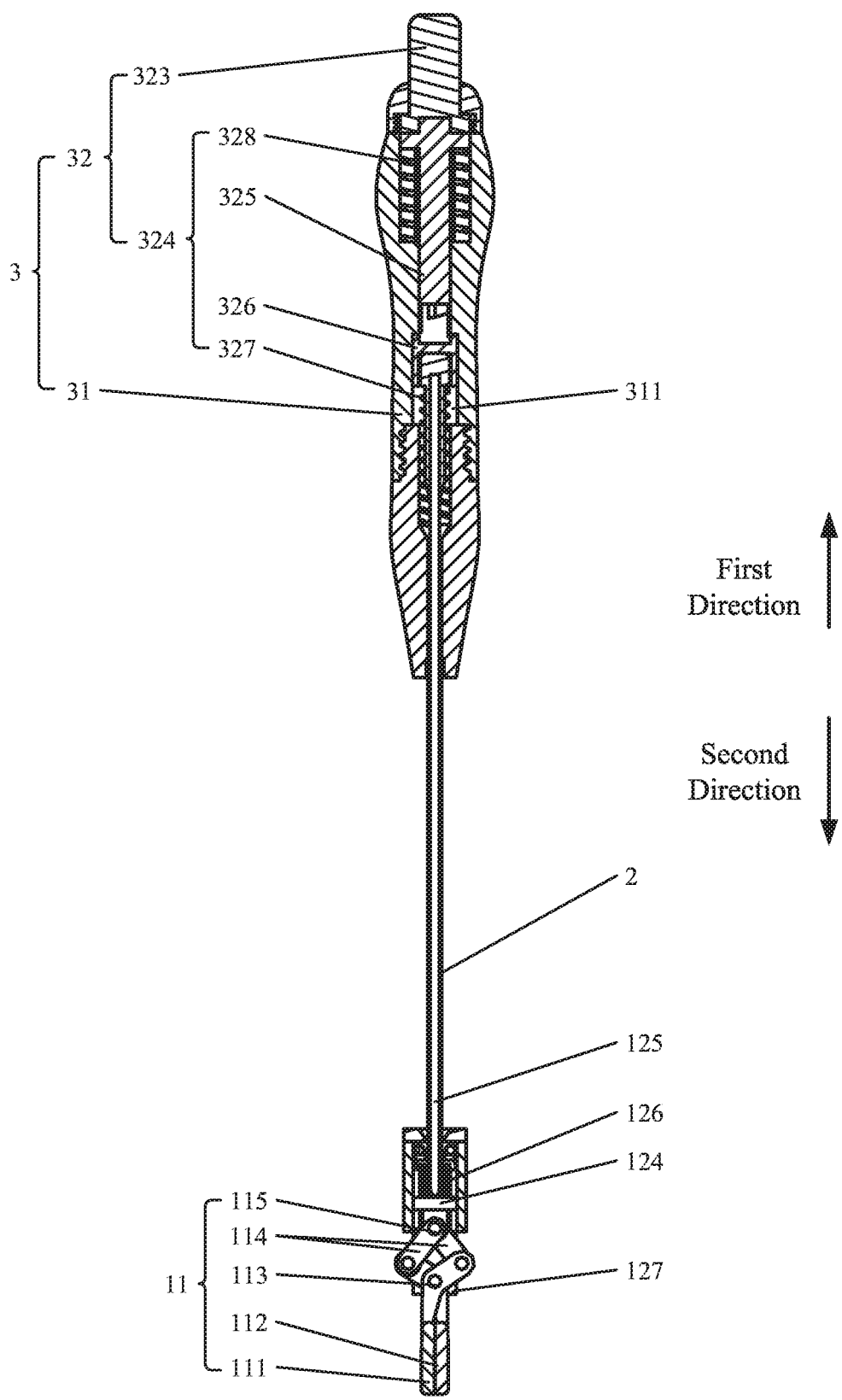
FIG. 14 is a diagram of an endoluminal surgery system according to the second embodiment of the present disclosure.

FIG. 14 is a schematic diagram of an endoluminal surgery system according to the embodiment of the present disclosure. As shown in FIG. 14, the endoluminal surgery system includes an operating device 1, a connecting rod 2 and a handle 3. In this embodiment of the present disclosure, a core rod may be arranged in the endoluminal surgery system, and the connecting rod 2 is a hollow needle 2. The operating device 1 is arranged in the thoracic or abdominal cavity for performing the corresponding operation on a lesion of the patient.

In the present embodiment, the operating device 1 includes an operating part 11 and a connecting part 12. The operating part 11 may be a surgical instrument adapted to for an endoluminal surgery, such as a retractor clamp, a pair of medical scissors, and the like. The connecting part 12 includes a fixing groove 121, a sliding groove 123, a slider 124 and a transmission component 125. In the present embodiment, the transmission component 125 is the core rod 125. The structure of the fixing groove 121, the structure of the hollow needle matched with the fixing groove 121, and the connection manner of the fixing groove 121 and the hollow needle are substantially the same as those in the first embodiment, which are not described here.

The sliding groove 123 and the slider 124 of the present embodiment may be the same as those in embodiment 1. The core rod 125 may be partly placed in the second channel 22 of the hollow needle 2, one end of the core rod 125 is configured to be in contact with the slider 124, and the other end is configured to be connected with the handle 3. The core rod 125 can be controlled to move along the second channel 22 so that the slider 124 can move along the sliding groove 123, thus controlling the operating part to perform the operation.

As shown in FIG. 15A to FIG. 17B, in the present embodiment, the operating part 11 is a retractor clamp 11, such as a lung clamp, a stomach clamp, an intestinal clamp, a liver clamp, a tendon clamp, a vascular clamp, and the like. The surgeon can choose a specific clamp according to the target tissue or organ. The retractor clamp 11 includes a first clamping arm 111 and a second clamping arm 112. The first clamping arm 111 and the second clamping arm 112 are rotatably connected through a first hinge shaft 113. The retractor clamp is also connected with the connecting part 12 through the first hinge shaft 113. The inner surface of the first clamping arm 111 and the inner surface of the second clamping arm 112 may be provided with antiskid strips to prevent the tissues or organs from slipping when the retractor clamp 11 is in the close state. Each of the tail of the first clamping arm 111 and the tail of the second clamping arm 112 is provided with a mounting hole. One of the two mounting holes is connected to an end of one of two connecting arms 114, and the other one of the two mounting holes is connected to an end of the other one of the two connecting arms 114. The other ends of the two connecting arms 114 are rotatably connected through a second hinge shaft 115.

The connecting part 12 may further include at least one connecting piece 127, which is arranged on the side of the connecting part 12 opposite to the sliding groove 123 and extends along the sliding groove 123. The connecting piece 127 is further provided with a connecting hole. The first hinge shaft 113 extends through the connecting hole and connects the retractor clamp 11 with the connecting part 12.

Figure 15A:
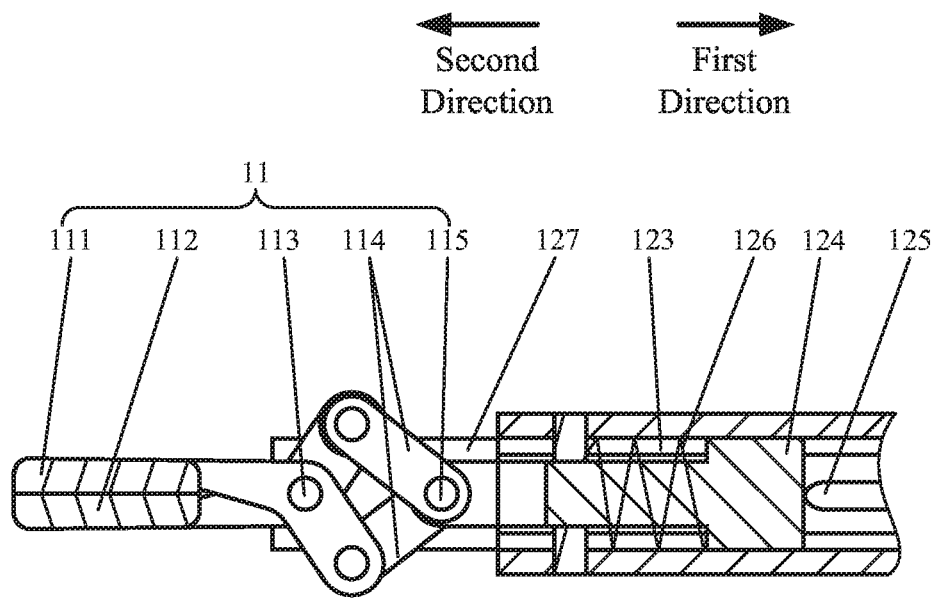
FIG. 15A is a schematic diagram of a first type operating device in a close state according to the second embodiment of the present disclosure.
Figure 15B:
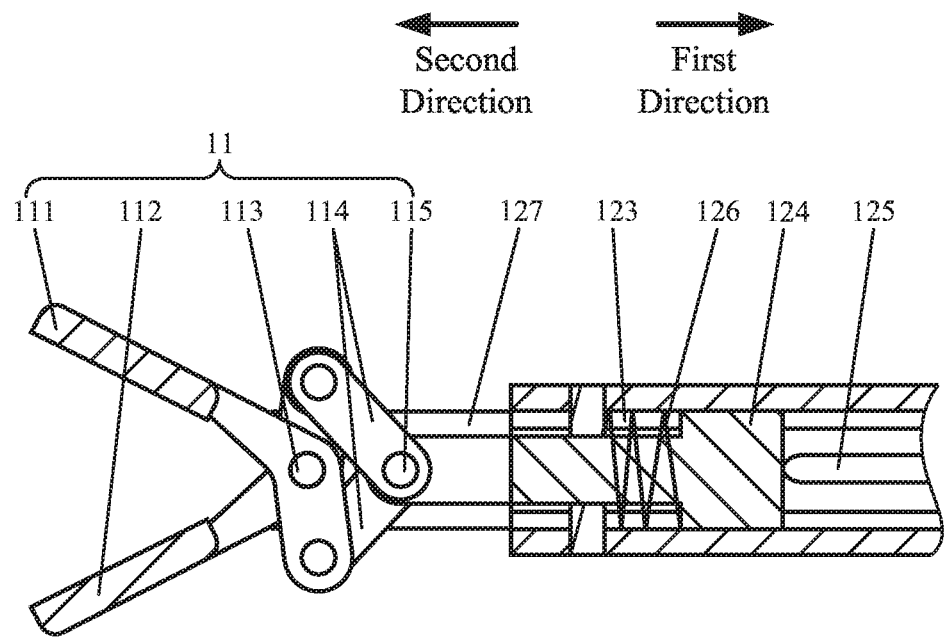
FIG. 15B is a schematic diagram of the first type operating device in an open state according to the second embodiment of the present disclosure.

As shown in FIG. 15A to FIG. 15B, the connecting part further includes a third elastic component 126, and a lug boss may be arranged at the end of the sliding groove 123 away from the fixing groove 121, and the third elastic component 126 is arranged between the lug boss and the slider 124. Two ends of the third elastic component 126 are fixedly connected with the lug boss and the slider 124 respectively. In the natural state (no external force is applied), an angle between the two connecting arms 114 is relatively small and the retractor clamp 11 is in a close state. When the core rod 125 pushes the slider 124 to move in the second direction, the third elastic component 126 is compressed, and the angle between the two connecting arms 114 gradually increases, which drives the first clamping arm 111 and the second clamping arm 112 to rotate relatively, and the retractor clamp is in an open state. However, when the core rod 125 is moved in the first direction, the slider 124 may be moved in the first direction under the action of the elasticity of the third elastic component 126, which drives the first clamping arm 111 and the second clamping arm 112 to rotate relatively, and the retractor clamp 11 may return to the natural state and clamp the target tissue or organ. The clamped tissue or organ is moved according to needs to provide a field of view required by the operation.

Figure 16A:
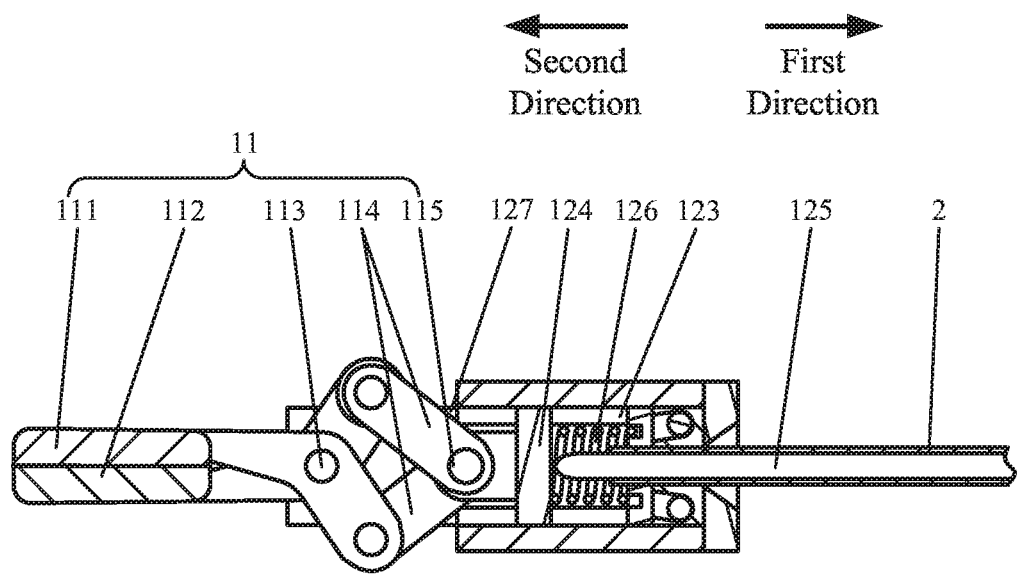
FIG. 16A is a schematic diagram of a second type operating device in a close state according to the second embodiment of the present disclosure.
Figure 16B:
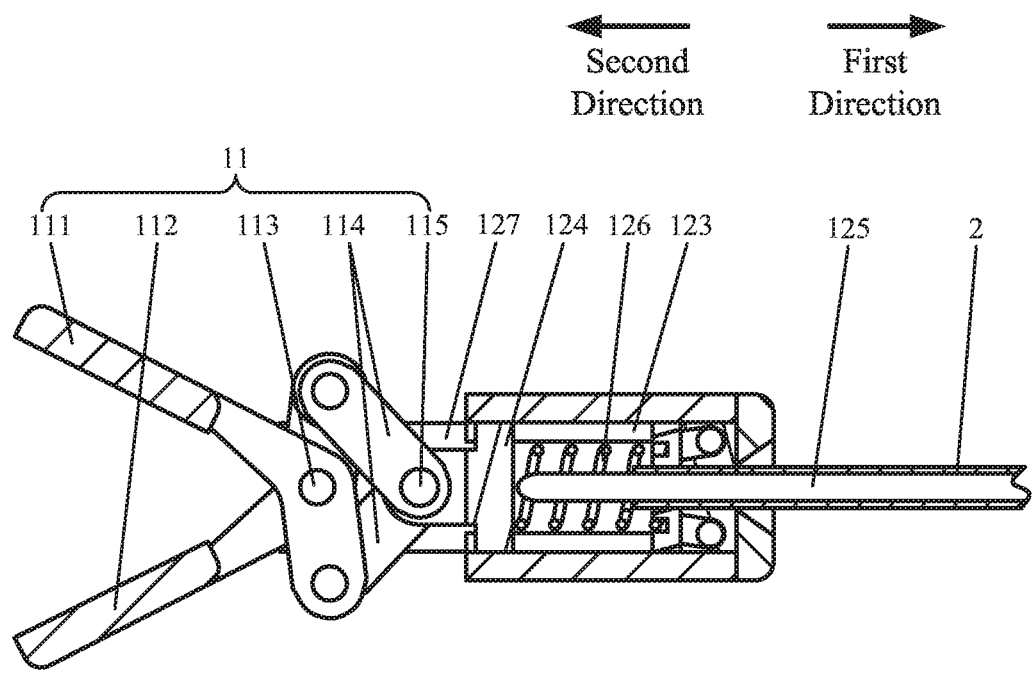
FIG. 16B is a schematic diagram of the second type operating device in an open state according to the second embodiment of the present disclosure.

As shown in FIG. 16A to FIG. 16B, in another implementation, a lug boss may be arranged at the end of the sliding groove 123 near the fixing groove 121, and a third elastic component 126 may be arranged in the accommodation space between the lug boss and the slider 124. The two ends of the third elastic component 126 are fixedly connected with the lug boss and the slider 124 respectively.

In the natural state (no external force is applied), an angle between the two connecting arms 114 is small and the retractor clamp 11 is in a close state. When the core rod 125 is pushed to move the slider 124 in the second direction, the third elastic component 126 is stretched, and the angle between the two connecting arms 114 gradually increases, which drives the first clamping arm 111 and the second clamping arm 112 to rotate relatively, so that the retractor clamp is in an open state. However, when the core rod 125 is moved in the first direction, the slider 124 is moved in the first direction under the action of the elasticity of the third elastic component 126, which drives the first clamping arm 111 and the second clamping arm 112 to rotate relatively, and the retractor clamp 11 may return to the natural state and clamp the target tissue or organ. The clamped tissue or organ is moved according to needs to provide a field of view required by the operation.

Figure 17A:
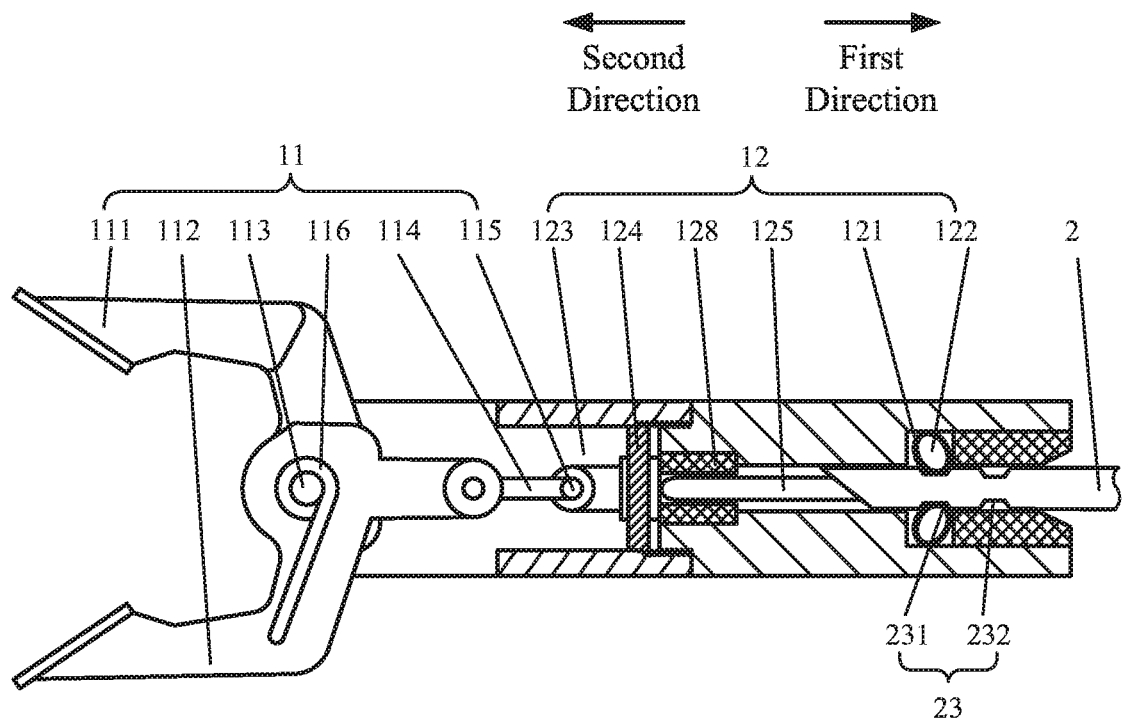
FIG. 17A is a schematic diagram of a third type operating device in an open state according to the second embodiment of the present disclosure.
Figure 17B:
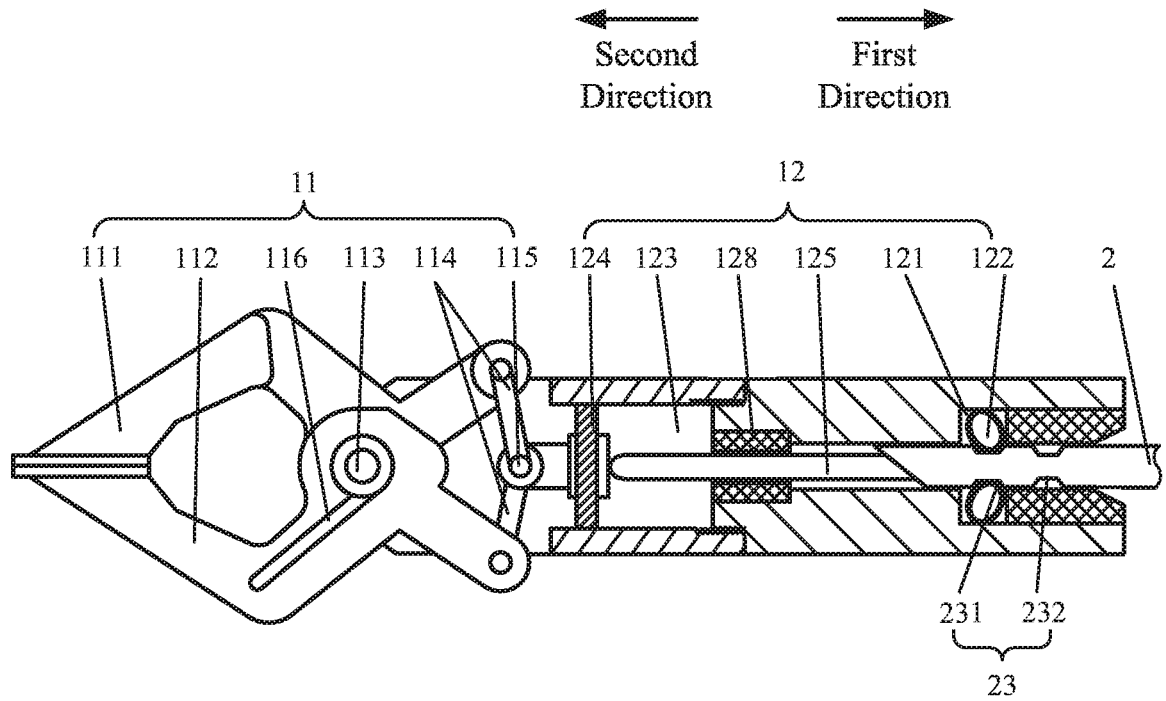
FIG. 17B is a schematic diagram of the third type operating device in a close state according to the second embodiment of the present disclosure.

As shown in FIG. 17A to FIG. 17B, in another implementation, the operating part 11 is a retractor clamp having a fourth elastic component 116, and the connecting part 12 does not include the third elastic component 126 according to needs. The retractor clamp 11 includes a first clamping arm 111 and a second clamping arm 112. The first clamping arm 111 and the second clamping arm 112 are rotatably connected through a first hinge shaft 113. The fourth elastic component 116 is disposed on the first hinge shaft 113. Two ends of the fourth elastic component 116 extend and are fixedly connected with the first clamping arm 111 and the second clamping arm 112 respectively. Further, the retractor clamp 11 may be also connected with the connecting part 12 through the first hinge shaft 113. The inner surface of the first clamping arm 111 and the inner surface of the second clamping arm 112 may be provided with antiskid strips to prevent the tissues or organs from slipping during the closing of the first and second clamping arms. Each of the tail of the first clamping arm 111 and the tail of the second clamping arm 112 is provided with a mounting hole. One of the two mounting holes is connected to an end of one of two connecting arms 114, and the other one of the two mounting holes is connected to an end of the other one of the two connecting arms 114. The other ends of the two connecting arms 114 are rotatably connected through a second hinge shaft 115. In the natural state, the retractor clamp is in the open state due to the elasticity of the fourth elastic component 116. When the core rod 125 pushes the slider 124 to move in the second direction, the angle between the two connecting arms 114 increases gradually, which drives the first clamping arm 111 and the second clamping arm 112 to rotate relatively, and the retractor clamp is in the close state, such that the target tissue or organ is clamped. The clamped tissue or organ is moved according to needs to provide a field of view required by the operation.

Optionally, if there is no need to manipulate the operating part 11 temporarily during the surgery, the operating part can be pulled to a position convenient for the surgery by pulling the handle 3 and the hollow needle 2 form outside, and is fixed by a vascular forceps at the skin, so as not to affect other surgery procedures in the cavity.

The outer diameter of the hollow needle 2 is typically less than 3 mm. In the surgery, the hollow needle 2 enters the cavity through the piercing point. After the hollow needle is pulled out, the formed piercing hole will recover on its own, and does no need to be sutured, which reduces the wound on the body surface by using a non-invasive. In the present embodiment, the hollow needle 2 includes a piercing end 21 and a fixed end. The piercing end 21 is configured to pierce into the body cavity D and be fixedly connect with the operating device 1. The piercing end 21 of the hollow needle 2 has an outer diameter of 2 mm, an inner diameter of 0.8 mm, and a length of about 100 mm. The fixed end is configured to be connected with the handle 3. An outer diameter of the fixed end is 10 mm and a length the fixed end is about 100 mm. Thus, the length of the most elongate part of the hollow needle 2 can be minimized, which enables the hollow needle 2 to withstand greater force and reduces the vibration of the piercing end 21. Preferably, the middle part of the piercing end 21 is provided with a frosted surface. The middle part of the piercing end 21 may include several parts in the longitudinal direction, each of which has a predetermined length and is provided with a frosted surface. Alternatively, the middle part is a frosted rod between the piercing end 21 and the fixed end, the frosted rod has a predetermined length, and two ends of the frosted rod are connected to the piercing end 21 and the fixed end respectively. The outer surface of the frosted rod is configured to be frosted. The outer diameter of the frosted rod is the same as that of the piercing end 21, and the inner diameter of the frosted rod is the same as that of the piercing end 21. The frosted rod, the piercing end 21, and the fixed end are coaxially arranged. The predetermined length may be to 10 mm, or the predetermined length can be designed according to different surgeries or different patients. After the hollow needle enters the cavity, the frosted surface can increase the friction between the hollow needle and the wall of the body cavity, increase the tightness of the contact between the hollow needle and the wall of the body cavity, and avoid air leakage during the laparoscopic surgery for not affecting the surgery procedures. In order to prevent the piercing end 21 of the hollow needle 2 from being damaged by the high strength and high hardness connecting part after the hollow needle 2 enters the fixing groove 121, a rubber protecting block 128 is arranged at the end of the fixing groove 121 to protect the piercing end 21 of the hollow needle 2. The rubber block 128 is provided with a hole to facilitate the pull line 125 to pass through. After the operation is finished, the hollow needle 2 is pulled out from the body of the patient, there is no scar at the piercing point, and no suturing is needed, so the non-invasive operation is achieved and the operation convenience is improved.

As shown in FIG. 14, the handle 3 includes a grip 31 and a control device 32, where the grip 31 is provided with a first channel 311. The grip 31 may be provided with a mounting hole for fixing the fixed end of the hollow needle 2. The control device 32 may include a button 323 and a transfer column 324. The transfer column 324 may be placed in the first channel 311 of the grip 31. One end of the button 323 is in contact with the transfer column 324, and the other end is outside the first channel 311. The operator may press the end outside the first channel 311 for performing control. At least a portion of the core rod 125 is accommodated in the second channel 22 of the hollow needle 2 and the first channel 311 of the grip 31, and the core rod 125 is in contact with the transfer column 324. Therefore, the button 323 can be operated outside the body to make the transfer column 324 move along the first channel 311 and be stopped at a specific position, the core rod 125 and the slider 124 are driven to move accordingly, so that the surgeon can control the operating device 1 by operating the handle 3.

In the present embodiment, the transfer column 324 may include an upper tooth column 325, a lower tooth column 326 and a first elastic component 327. The end of the core rod 125 located in the first channel 311 may be provided with a base whose diameter is larger than that of the core rod 125. The first elastic component 327 is arranged around the core rod 125 and supported between the base 321 of the core rod 125 and the lug boss in the first channel 311 of the grip 31, so that the core rod 125 and the transfer column 324 are kept in a movement trend in the first direction. The upper tooth column 325 is provided with a first tooth part, while the lower tooth column 326 is provided with a second tooth part. The first tooth part and the second tooth part are placed oppositely and can be engaged with each other at one or more positions. Moreover, the transfer column 324 further includes a second elastic component 328, which is placed in the first channel 311 and is in contact with the upper tooth column 325 for making the upper tooth column 325 be kept in a movement trend in the second direction.

Figure 18:
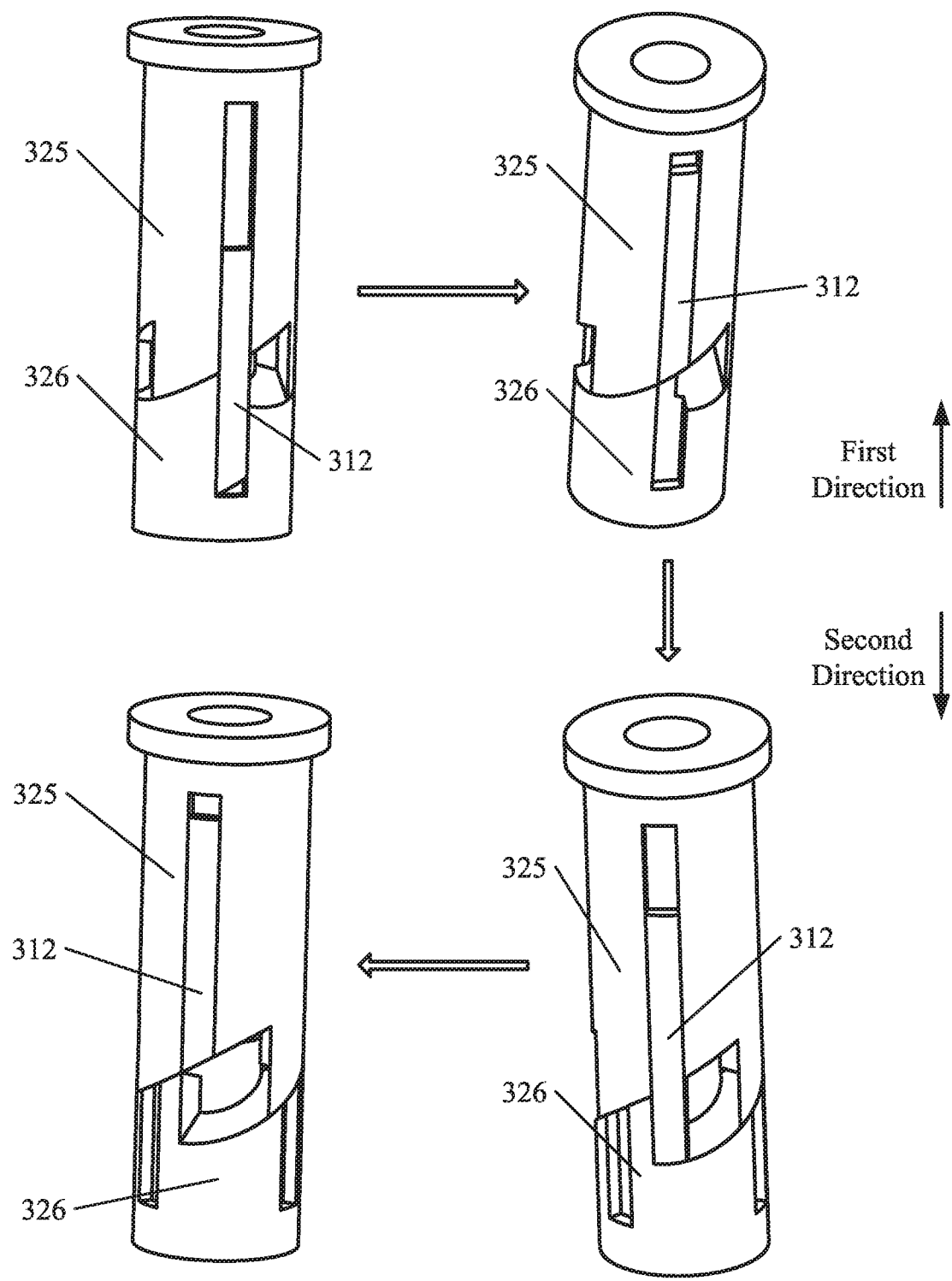
FIG. 18 is a first schematic diagram illustrating a principle of a control device of the endoluminal surgery system according to the second embodiment of the present disclosure.
Figure 19:
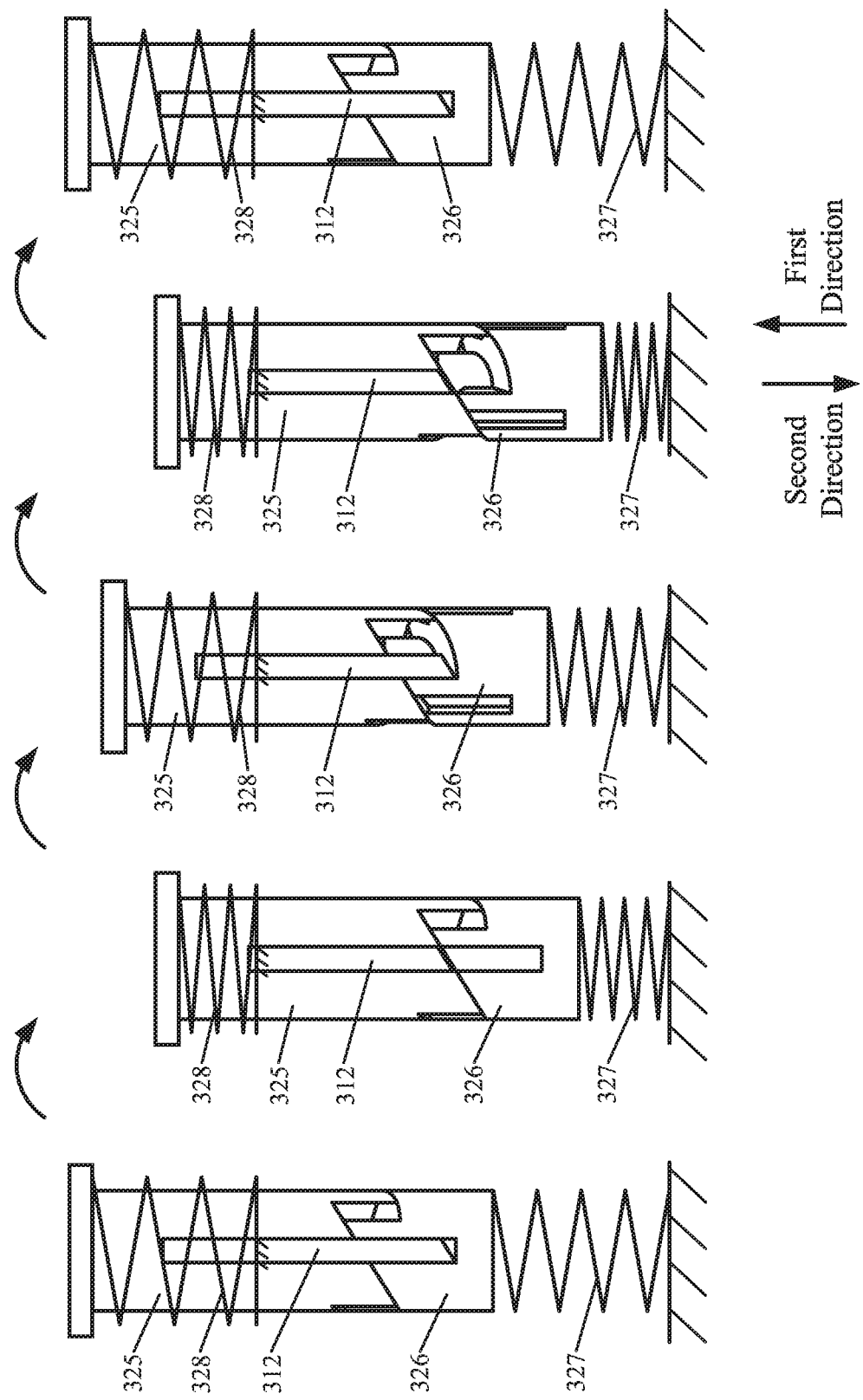
FIG. 19 is a second schematic diagram illustrating a principle of a control device of the endoluminal surgery system according to the second embodiment of the present disclosure.

As shown in FIG. 18 and FIG. 19, in an optional implementation, three protruding guide rails 312 may be uniformly distributed in the circumference of the first channel 311 of the grip 31. Each guide rail 312 has a first end and a second end. The first end is a slope. In the following description of the working principle of the control device 32, the operating part 11 is the retractor clamp, and the open angle of the retractor clamp is increased when the slider 124 moves towards the second direction. The grip 31 may be regarded as a stationary reference basis, and the guide rails 312, the end of the first elastic component 327 in contact with the lug boss of the grip 31 and the end of the second elastic component 328 in contact with the guide rails 312 are regarded as stationary.

The first tooth part is three teeth and three guide rail grooves distributed in the circumferential direction, and each of three guide rail grooves corresponds to the second end of a respective one of the guide rails 312. The second tooth part is three teeth and three guide rail grooves distributed in the circumferential direction, and each of the three guide rail grooves corresponds to the first end of a respective one of the guide rails 312. The positions of the guide rail grooves of the upper tooth column 325 are different from that of the lower tooth column 326. The first tooth part and the second tooth part can be engaged with each other, and the slopes of the first ends of the guide rails 312 can be engaged with the second tooth part. The second elastic component 328 is externally fitted at the outer periphery of the upper tooth column 223 and supported between the upper tooth column 325 and the second ends of the guide rails 312 of the grip 31, so that the upper tooth column 325 can be kept in a movement trend in the first direction. The button 323 is connected with the upper tooth column 325. When the control device 32 is in the natural state (the state in which no external force is applied), the first end of each of the guide rails 312 is in the corresponding guide rail groove of the lower tooth column 326, the second end of each of the guide rails 312 is in the corresponding guide rail groove of the upper tooth column 325, and the first tooth part of the upper tooth column 325 is engaged with the second tooth part of the lower tooth column 326, at this time, the retractor clamp is in the close state. When an external force is applied to the button 323 and causes the button 323 to move in the second direction, the upper tooth column 325 also moves along the guide rails 312 towards the second direction, and the lower tooth column 326 is pushed to move along the guide rails 312 towards the second direction until the engaging surfaces of the upper tooth column 325 and the lower tooth column 326 are in the same plane as the slope of the first end of the guide rail 312, that is, the first ends of the guide rails 312 leave the guide rail grooves of the lower tooth column 326. In the above process, the core rod 125 moves towards the second direction, pushes the slider 124 to move towards the second direction, thus controlling the opening angle of the retractor clamp 11 to gradually increase. Meanwhile, the first elastic component 327 and the second elastic component 328 are both compressed. When the engaging surfaces of the upper tooth column 325 and the lower tooth column 326 are in the same plane as the slope of the first end of the guide rail 312, if the external force applied on the button 323 is reduced or removed, the lower tooth column 326 moves rotationally along the engaging surface towards the first direction because of the elasticity of the first elastic component 327 towards the first direction, and at the same time, the upper tooth column 325 moves towards the first direction along the guide rails 312 because of the elasticity of the second elastic component 328. In the above process, the core rod 125 and the slider 124 both move towards the first direction until the teeth of the lower tooth column 326 are rotated by a predetermined angle, engaged with the teeth of the upper tooth column 325, and stopped at the guide rails 312, which eventually makes the control device 32 be in a locked state. The control device 32 in the locked state causes the retractor clamp 11 to be opened with a small fixed angle and clamp the target tissue or organ, and the first elastic component 327 is still in a compressed state. When the external force is applied on the button 323 again, the upper tooth column 325 moves towards the second direction along the guide rails 312, and pushes the lower tooth column 326 to move towards the second direction along the guide rails 312 until the engaging surfaces of the upper tooth column 325 and the lower tooth column 326 are in the same plane as the slope of the first end of the guide rail 312. In the above process, the core rod 125 moves towards the second direction, the open angle of the retractor clamp 11 increases, so that the target tissue or organ is released, and the first elastic component 327 and the second elastic component 328 are further compressed. When the engaging surfaces of the upper tooth column 325 and the lower tooth column 326 are in the same plane as the slope of the first end of the guide rail 312, if the external force applied on the button 323 is reduced or removed, because of the elasticity of the first elastic component 327 towards the first direction, the lower tooth column 326 rotationally moves towards the first direction along the engaging surface until the first ends of the guide rails 312 are in the guide rail grooves of the lower tooth column 326. Meanwhile, the upper tooth column 325 moves towards the first direction along the guide rails 312 because of the elasticity of the second elastic component 328. In the above process, the core rod 125 moves in the first direction for a predetermined distance and the open angle of the retractor clamp 11 decreases until to approximately zero, that is, the control device 32 returns to the natural state.

In another optional implementation, those skilled in the art may adopt a motor to drive the transfer column 324. The control device 32 includes a button 323, a transfer column 324 and a motor. The transfer column 324 is provided with threads in its circumferential direction, the inner wall of the first channel 311 of the grip 31 is provided with corresponding threads. The output shaft of the motor is connected with the transfer column 324 and can drive the transfer column 324 to rotate. The motor housing and the grip rod 31 are slidably connected, for example, a groove is arranged in the first channel 311 of the grip rod 31, and a guide block is arranged in the corresponding position on the motor housing, so that the motor can slide along the guide groove in the first channel 311. The button 323 is electrically connected with the motor and can control the motor to rotate the output shaft forwardly or reversely. When the output shaft of the motor is controlled by the button 323 to rotate in one direction, the transfer column 324 rotates along the threads of the first channel 311 and moves towards the second direction, the core rod 125 also moves in the second direction and finally stops at a first position, and the retractor clamp 11 is in an open state. When the output shaft of the motor is controlled to rotate in the other direction, the transfer column 324 rotates along the threads of the first channel 311 and moves towards the first direction, the core rod 125 also moves in the first direction and finally stops at a second position, and the retractor clamp 11 is in a close state.

Figure 20:
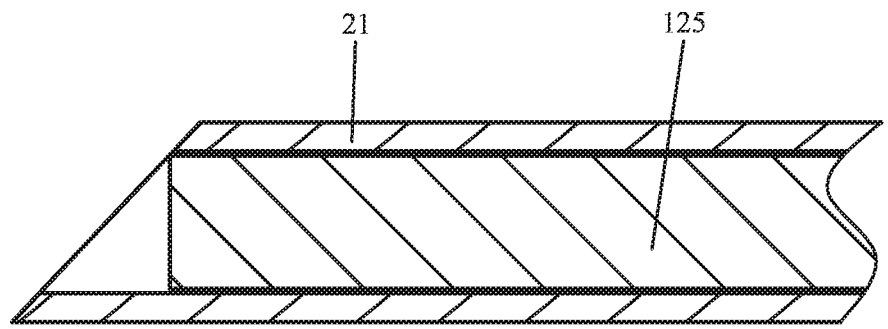
FIG. 20 is a first structural diagram of a piercing end of a connecting rod and a head of a core rod according to the second embodiment of the present disclosure.
Figure 21:
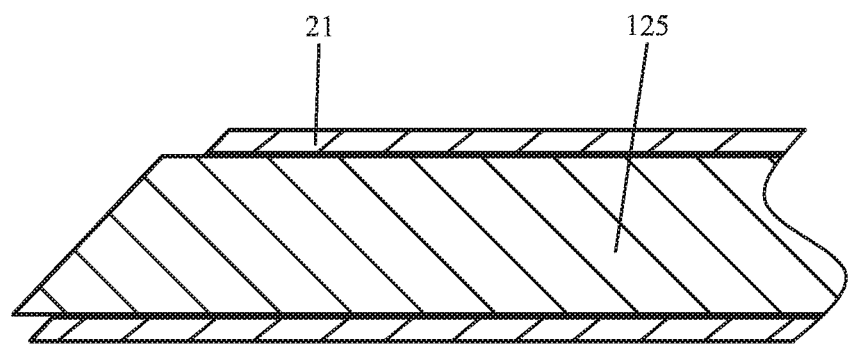
FIG. 21 is a second structural diagram of a piercing end of a connecting rod and a head of a core rod according to the second embodiment of the present disclosure.
Figure 22:
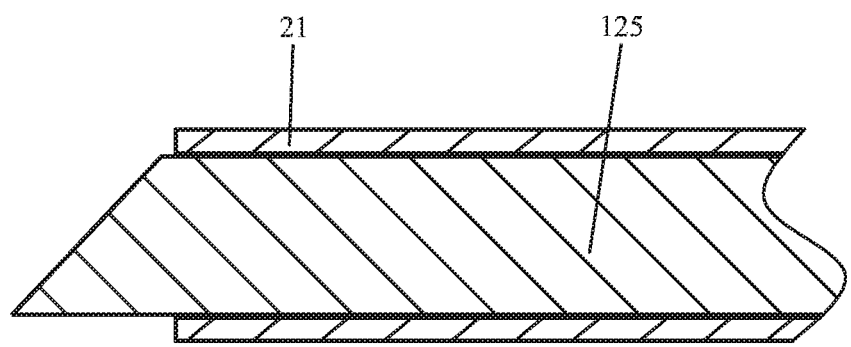
FIG. 22 is a third structural diagram of a piercing end of a connecting rod and a head of a core rod according to the second embodiment of the present disclosure.

As shown in FIG. 20 to FIG. 22, the size of the connecting rod 2 and the size of the core rod 125 should match each other. At least one of the piercing end 21 of the connecting rod 2 and the head of the core rod 125 shall be provided with a tip so as to pierce into the body cavity through the skin, where the head of the core rod 125 is the end used for piercing into the body cavity.

As shown in FIG. 20, in an optional implementation, the piercing end 21 of the connecting rod 2 is provided with a tip, while the head of the core rod 125 is not provided with a tip. When piercing into the cavity, the head of the core rod 125 should be accommodated in the second channel 22 of the connecting rod 2, and the tip of the connecting rod 2 pierces into the cavity through the skin.

As shown in FIG. 21, in another optional implementation, each of the piercing end 21 of the connecting rod 2 and the head of the core rod 125 is provided with a tip. In this implementation, the head of the connecting rod is outside the piercing end 21 of the connecting rod 2, the head of the connecting rod pierces into the body cavity through the skin first, and then the piercing end 21 of the connecting rod 2 pierces into the body cavity through the skin. Alternatively, the head of the connecting rod is accommodated in the second channel 22, and the piercing end 21 of the connecting rod 2 pierces into the body cavity through the skin.

As shown in FIG. 22, in another optional implementation core rod, the head of the core rod 125 is provided with a tip, while the piercing end 21 of the connecting rod 2 is not provided with a tip. When the connecting rod 2 pierces into the body cavity, the head of the core rod is exposed out of the piercing end 21 of the connecting rod 2, core rod the head of the core rod 125 is pierced into the body cavity firstly, and then the piercing end 21 of the connecting rod 2 can enter the body cavity through the piercing hole of the core rod 125. In this case, the difference between the outer diameter of the connecting rod 2 and the diameter of the core rod 125 should not be too large as to prevent the connecting rod 2 from being blocked.

During the operation, the surgeon makes an incision B on the patient's body surface A according to needs, and then inserts a trocar C corresponding to the size of the incision through the incision B to form an entry and exit passage for the surgical instrument. Then, the surgeon places the operating device 1 through the trocar C into the body cavity D. The surgeon makes the handle 3 and the hollow needle 2 fixedly connected, and pierces the hollow needle 2 into the patient's body cavity D through a selected piercing point on the patient's body surface A. The hollow needle 2 is fixedly connected with the connecting part 12. By pressing the button 323, the head of the core rod 125 can be moved in the connecting part 12 so as to control the retractor clamp to clamp the target organ. If necessary, multiple operating devices 1 can be placed in the body cavity D so as to clamp different positions of the target organ for better exposing the operation position. At the end of the surgery, the head of the core rod is adjusted through the control device 32 so as to control the retractor clamp to unclamp, and then core rod the hollow needle 2 is separated from the connecting part 12 of the operating device 1. The hollow needle 2 and the core rod are pulled out from the body, and the operating device 1 is taken out from the body through the trocar C. The incision is sutured to finish the operation. In another implementation, the hollow needle 2 and the core rod are directly cut off together, and the hollow needle 2, the core rod, and the operating device in the body cavity are taken out from the body through the incision. The endoluminal surgery system of the present embodiment is a non-invasive surgery system and can reduce the injury to the body of the patient. Furthermore, the operating device is controlled through the button 323 disposed outside the body, there is no need to lead out the pull line by using the hook needle, so it is more conveniently to perform the operation outside the body.

Third Embodiment

Figure 23A:
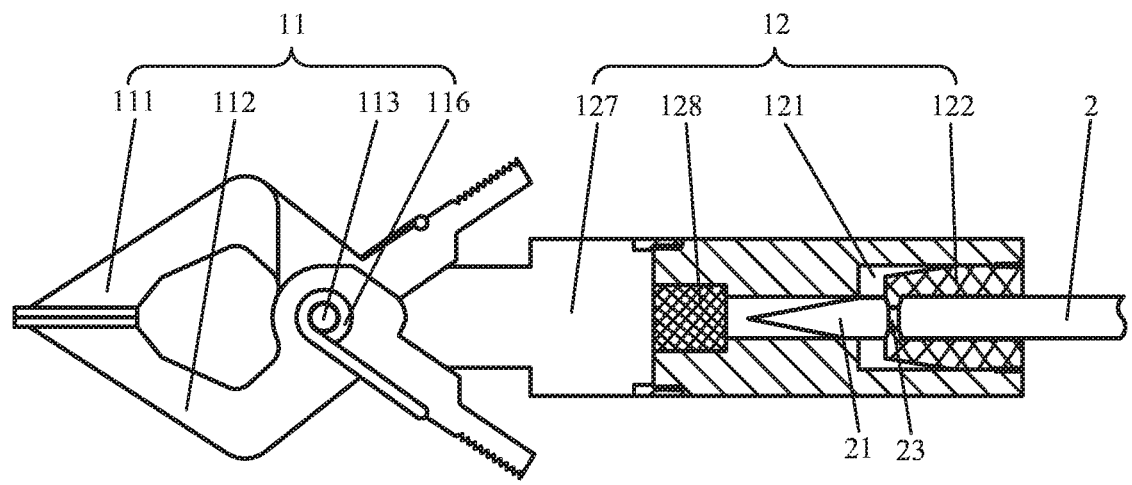
FIG. 23A is a structural diagram of an operating device in an open state according to the third embodiment of the present disclosure.
Figure 23B:
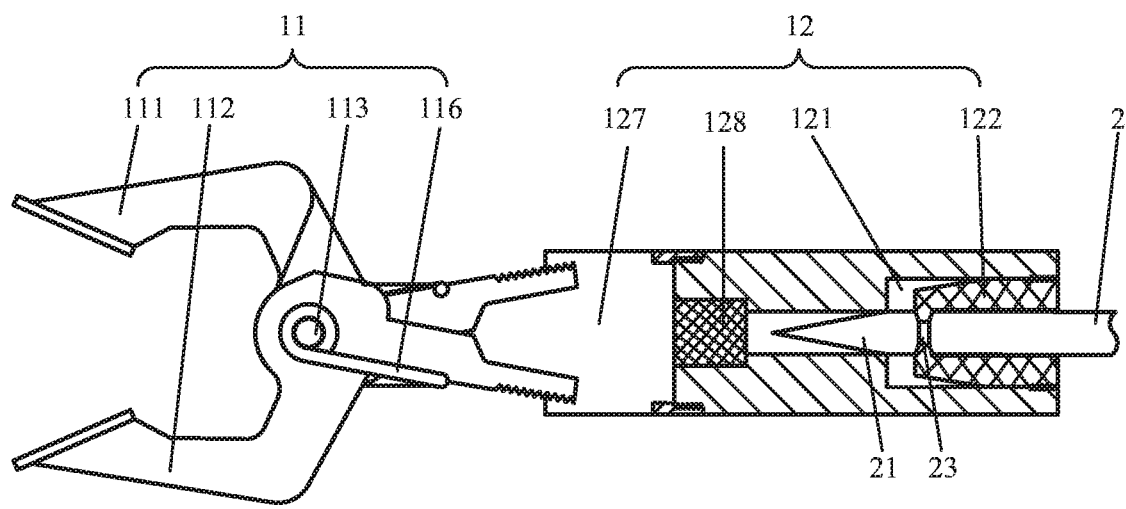
FIG. 23B is a structural diagram of the operating device in a close state according to the third embodiment of the present disclosure.

FIG. 23A and FIG. 23B are structural diagrams illustrating an operating device according to the third embodiment of the present disclosure. The endoluminal surgery system includes an operating device 1, a connecting rod 2 and a handle 3. In the present embodiment, the connecting rod 2 may be a solid needle or a hollow needle, and includes a piercing end 21. The piercing end 21 is provided with a tip for piercing into a body. The handle 3 may be provided with a mounting hole or other connecting device for fixing the connecting rod 2.

As shown in FIG. 23A and FIG. 23B, the operating device 1 includes an operating part 11 and a connecting part 12. The operating part 11 may be a retractor clamp, a medical scissor or other surgical instrument suitable for an endoscopic surgery.

In the present embodiment, the operating part 11 is a retractor clamp 11, such as a lung clamp, a stomach clamp, an intestinal clamp, a liver clamp, a tendon clamp, a vascular clamp, and the like. The surgeon can choose a specific clamp according to the target tissue or organ. Specifically, in the present embodiment, the operating part 11 is a retractor clamp having a spring. The retractor clamp 11 includes a first clamping arm 111 and a second clamping arm 112. The first clamping arm 111 and the second clamping arm 112 are rotatably connected through a first hinge shaft 113. The first hinge shaft 113 is provided with a fourth elastic component 116. Two ends of the fourth elastic component 116 extend and are fixedly connected with the first clamping arm 111 and the second clamping arm 112 respectively. in the natural state (the state in which no external force is applied) the retractor clamp is in the close state due to the elasticity of the fourth elastic component 116. The inner surface of the first clamping arm 111 and the inner surface of the second clamping arm 112 may be provided with antiskid strips according to needs, which can prevent the tissue or organ from slipping As shown in FIG. 23A and FIG. 23B, the connecting part 12 includes a fixing groove 121 and a connecting piece 127. A first limiting part 122 for fixing the connecting rod 2 is arranged in the fixing groove 121. The piercing end 21 of the connecting rod 2 is provided with a second limiting part 23 matched with the first limiting part 122. When the piercing end 21 of the connecting rod 2 enters the fixing groove 121, the connecting rod 2 and the connecting part 12 are fixedly connected through the first limiting part 122 and the second limiting part 23. The connecting part 12 can be made of materials with high strength such as alloy steel, which can improve the strength of the operating device 1, and can also used for manufacturing small size structures to meet usage requirements.

In the present embodiment, the first limiting part 122 may be an elastic jaw, and the elastic jaw is embedded in the fixing groove 121 and fixedly connected with an end of the fixing groove 121. The second limiting part 23 is a clamping groove 231. After the connecting rod 2 enters the body cavity through the piercing point, due to the elasticity of the jaw, the jaw moves at the piercing end 21 of the connecting rod 2. When the jaw moves to the clamping groove 231, since the accommodating space is larger, the jaw returns to its natural state and is fixedly connected with the clamping groove 231.

In another optional implementation, the first limiting part 122 and the second limiting part 23 may be configured in other structures, which are basically the same as other first limiting part 122 and second limiting part 23 in the first embodiment and will not be repeated below.

The connecting piece 127 is arranged on the side of the connecting part 12 opposite to the fixing groove 121 and extends along the fixed groove 121. The connecting piece 127 is further provided with a connecting hole. The first hinge shaft 113 extends through the connecting hole and fixedly connected the retractor clamp and the connecting part 12.

In the present embodiment, in the surgery, the outer diameter of the connecting rod is generally less than 3 mm. The connecting rod 2 includes the piercing end 21 and the fixed end, The piercing end 21 is configured to pierce into the body cavity and be fixedly connected with the operating device 1. The outer diameter of the piercing end 21 of the connecting rod 2 is 2 mm, and the length of the piercing end 21 is about 100 mm. The fixed end is configured to be mounted with the handle 3. The outer diameter of the fixed end of the connecting rod 2 is 10 mm, and the length of the fixed end is 100 mm. In this way, the length of the most elongate part of the connecting rod 2 can be minimized, the connecting rod 2 can withstand a greater force, and the vibration of the piercing end 21 is reduced. Preferably, the middle part of the piercing end 21 is provided with a frosted surface. The middle part of the piercing end 21 may include several parts in the longitudinal direction, each of which has a predetermined length and is provided with a frosted surface. Alternatively, the middle part is a frosted rod between the piercing end 21 and the fixed end, the frosted rod has a predetermined length, and two ends of the frosted rod are connected to the piercing end 21 and the fixed end respectively. The outer surface of the frosted rod is configured to be frosted. The outer diameter of the frosted rod is the same as that of the piercing end 21, and the inner diameter of the frosted rod is the same as that of the piercing end 21. The frosted rod, the piercing end 21, and the fixed end are coaxially arranged. The predetermined length may be to 10 mm, or the predetermined length can be designed according to different surgeries or different patients. After the connecting rod enters the cavity, the frosted surface can increase the friction between the connecting rod and the wall of the body cavity, increase the tightness of the contact between the connecting rod and the wall of the body cavity, and avoid air leakage during the laparoscopic surgery for not affecting the surgery procedures. In order to prevent the piercing end 21 of the connecting rod 2 from being damaged by the high strength and high hardness connecting part 2 after the connecting rod 2 enters the fixing groove 121, a rubber protecting block 128 is arranged at the end of the fixing groove 121 to protect the piercing end 21 of the hollow needle 2.

During the operation, the surgeon makes an incision B on the patient's body surface A according to needs, and then inserts a trocar C corresponding to the size of the incision through the incision B to form an entry and exit passage for the surgical instrument. Then, the surgeon places the operating device 1 through the trocar C into the body cavity D. The surgeon pierces the connecting rod 2 that is fixedly mounted with the handle 3 into the patient's body cavity through a selected piercing point on the patient's body surface, and sends a separation forceps into the cavity through the incision B. The separation forceps clamps extending ends of the first clamping arm 111 and the second clamping arm 112, where the first clamping arm 111 and the second clamping arm 112 are connected to two ends of the fourth elastic component 116 respectively. The retractor clamp is unclamped and placed at the target tissue or organ, and then the separation forceps is loosed, so that the retractor clamp returns to the natural state due to the elasticity of the fourth elastic component 116 and clamps the target tissue or organ. The connecting rod 2 is fixed connected with the connecting part 12 of the operating device 1. The retractor clamp is controlled through the handle 3 to move the organ that needs to be exposed. Then, the length of the connecting rod 2 in the body is adjusted through the handle 3 to achieve the precise exposing of the organ. After the surgery is complete, the connecting rod 2 is cut off, the operating device 1 is taken out of the body through the incision. The endoluminal surgery system in the present embodiment can reduce the damage to the patients and can facilitate the control of the retracting force and the retracting direction from outside of the body.

The endoluminal surgery system of embodiments of the present embodiment includes: an operating device, a handle and a connecting rod. The operating device includes an operating part and a connecting part. During the surgery, the operating device can be placed in the body cavity through the incision, and the piercing end 21 of the connecting rod enters the body cavity through the piercing point and is fixedly connected with the connecting part of the operating device. The other end, outside the body, of the connecting rod is connected with the handle. Then, the operating part can be controlled and adjusted through the handle outside the body to achieve the corresponding surgery procedures. The present disclosure provides a non-invasive or minimally invasive way to reduce the injury to the patient's body, makes the surgical procedures outside the body more convenient, and improves the success rate of the operation.

The above description is only preferred embodiments of the present invention and is not intended to limit the present invention. For those skilled in the art, the present invention may have various modifications and changes. Any modification, equivalent replacement, improvement, etc. made within the spirit and principle of the present invention shall be included in the protection scope of the present invention.

The invention claimed is:

1. An endoluminal surgery system, comprising:
   an operating device comprising an operating part and a connecting part;
   a connecting rod comprising a piercing end adapted to pierce into a body cavity; and
   a handle for fixing the connecting rod;
   wherein the connecting part is configured to be fixedly connected with the piercing end of the connecting rod in the body cavity;

wherein the connecting part comprises:
  a fixing groove for accommodating the piercing end of the connecting rod, wherein a first limiting part for fixing the connecting rod is arranged in the fixing groove, wherein the piercing end of the connecting rod is provided with a second limiting part matched with the first limiting part;
  a sliding groove arranged opposite to the fixing groove;
  a slider arranged in the sliding groove, wherein the slider and the operating part are connected; and
  a transmission component configured to control movement of the slider in the sliding groove to change a working state of the operating part.

2. The endoluminal surgery system according to claim 1, wherein the handle comprises:
  a grip with a first channel inside, wherein the first channel is used for accommodating at least a portion of the transmission component, and the grip is fixedly connected with the connecting rod; and
  a control device configured to be connected with the transmission component and control movement of the transmission component.

3. The endoluminal surgery system according to claim 2, wherein the connecting rod is provided with a hollow second channel, and the first channel is aligned with the second channel;
  the transmission component is a pull line, wherein one end of the pull line is fixedly connected with the slider, and the other end of the pull line passes through the second channel and is connected with the control device, wherein the slider moves in response to being pulled by the pull line.

4. The endoluminal surgery system according to claim 3, further comprising:
  a hook needle, wherein an end of the hook needle is provided with a groove or a hook.

5. The endoluminal surgery system according to claim 2, wherein the connecting rod is provided with a hollow second channel, and the first channel is aligned with the second channel;
  the transmission component is a core rod in particular, wherein the core rod is partially in the second channel of the connecting rod, one end of the core rod is in contact with the slider, and the other end of the core rod is in contact with the control device.

6. The endoluminal surgery system according to claim 5, wherein the control device comprises:
  a button for transmitting a force of a user; and
  a transfer column arranged in the first channel, wherein one end of the transfer column is in contact with the core rod, the transfer column is configured to move along the first channel according to the force exerted on the button so as to cause the core rod to move along the second channel.

7. The endoluminal surgery system according to claim 6, wherein the transfer column comprises:
  an upper tooth column with a first tooth part;
  a lower tooth column with a second tooth part; and
  a first elastic component arranged in the first channel, wherein the first elastic component is configured to cause the core rod and the lower tooth column to keep a motion trend in a first direction;
  wherein the first tooth part and the second tooth part are disposed to face each other, and are configured to be engaged with each other in at least one position.

8. The endoluminal surgery system according to claim 7, wherein the transfer column further comprises:
  a second elastic component arranged in the first channel and in contact with the upper tooth column, wherein the second elastic component is configured to cause the upper tooth column to keep a motion trend in the first direction.

9. The endoluminal surgery system according to claim 1, wherein the connecting part further comprises:
  a third elastic component connected with the slider, wherein the third elastic component is configured to cause the slider to keep a motion trend in the first direction, or cause the slider to keep a motion trend in a second direction.

10. The endoluminal surgery system according to claim 1, wherein the connecting part further comprises: a connecting piece, wherein the connecting piece extends along a side of the sliding groove; and
  the operating part is a retractor clamp in particular, wherein the retractor clamp is connected with the connecting piece.

11. The endoluminal surgery system according to claim 10, wherein the retractor clamp comprises a first clamping arm and a second clamping arm, wherein the first clamping arm and the second clamping arm are rotatably connected by a first hinge shaft;
  the first hinge shaft is fixedly connected with the connecting piece.

12. The endoluminal surgery system according to claim 11, wherein the first hinge shaft is provided with a fourth elastic component, two ends of the fourth elastic component extend and are fixedly connected with the first clamping arm and the second clamping arm respectively.

13. The endoluminal surgery system according to claim 1, wherein the first limiting part is a buckle, and the second limiting part is a clamping groove.

14. The endoluminal surgery system according to claim 1, wherein the first limiting part and the second limiting part are threads.

15. The endoluminal surgery system according to claim 1, wherein the first limiting part comprises at least one elastic ring, and the second limiting part is provided with a clamping groove and a guide groove, wherein the clamping groove and the guide groove are matched with the elastic ring; wherein the connecting rod is fixed with the elastic ring by the clamping groove, and separated from the elastic ring by the guiding groove.

16. The endoluminal surgery system according to claim 1, wherein the first limiting part is provided with a through-hole, a fixing buckle is provided in the through-hole and is configured to fix the connecting rod;
  wherein the first limiting part is fixedly connected with the fixing groove by a fifth elastic component;
  the second limiting part is a clamping groove;
  in a first state, the through-hole of the first limiting part is coaxially disposed with the fixing groove to make the connecting rod go through the through-hole; and
  in a second state, the buckle in the through-hole is engaged with the clamping groove to fix the connecting rod.

17. The endoluminal surgery system according to claim 1, wherein the first limiting part is an elastic jaw; and
  the second limiting part is a clamping groove, wherein the clamping groove is fixedly connected with the jaw to fix the connecting rod.

18. The endoluminal surgery system according to claim 1, wherein the piercing end is provided with a tip.

* * * * *